US012583845B2

(12) United States Patent
Mazdiyasni et al.

(10) Patent No.: US 12,583,845 B2
(45) Date of Patent: Mar. 24, 2026

(54) COMPOSITIONS AND METHODS FOR TREATING DISEASES, DISORDERS AND CONDITIONS INVOLVING TRINUCLEOTIDE REPEATS

(71) Applicant: The Research Foundation for the State University of New York, Albany, NY (US)

(72) Inventors: Hormoz Mazdiyasni, Menands, NY (US); John Andrew Berglund, Menands, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 17/959,826

(22) Filed: Oct. 4, 2022

(65) Prior Publication Data

US 2023/0117938 A1 Apr. 20, 2023

Related U.S. Application Data

(60) Provisional application No. 63/252,101, filed on Oct. 4, 2021.

(51) Int. Cl.

| | |
|---|---|
| ***C07D 405/14*** | (2006.01) |
| ***A61P 21/00*** | (2006.01) |
| ***C07D 307/52*** | (2006.01) |
| ***C07D 403/14*** | (2006.01) |
| ***C07D 409/14*** | (2006.01) |
| ***C07D 471/04*** | (2006.01) |
| ***C07D 487/04*** | (2006.01) |

(52) U.S. Cl.

CPC ............ *C07D 405/14* (2013.01); *A61P 21/00* (2018.01); *C07D 307/52* (2013.01); *C07D 403/14* (2013.01); *C07D 409/14* (2013.01); *C07D 471/04* (2013.01); *C07D 487/04* (2013.01)

(58) Field of Classification Search

CPC .................................................... C07D 405/14

See application file for complete search history.

(56) References Cited

U.S. PATENT DOCUMENTS

2012/0010176 A1* 1/2012 Khurana ................. A61P 21/00 514/378

OTHER PUBLICATIONS

Rohilla and Gagnon "RNA biology of disease-associated microsatellite repeat expansions" Acta Neuropathologica Communications (2017) 5:63.*

Thomas "Targeting RNA with Small Molecules" Chemical Reviews, 2008, vol. 108, No. 4 1172-1224.*

Bevilacqua "Genome-Wide Analysis of RNA Secondary Structure" Annu. Rev. Genet. 2016. 50:235-66.*

Tran "Identifying the preferred RNA motifs and chemotypes that interact by probing millions of combinations" Nature communications (2012), 3, 1125.*

Haniff "Selective Small Molecule Recognition of RNA Base Pairs" : ACS Comb. Sci. 2018, 20, 482-491.*

Angelbello "Small molecule targeting of RNA structures in neurological disorders" Ann. N.Y. Acad. Sci. 1471 (2020) 57-71, Figure 6.*

* cited by examiner

*Primary Examiner* — David K O'Dell

(74) *Attorney, Agent, or Firm* — Peter Fallon

(57) ABSTRACT

The present disclosure provides compositions that inhibit microsatellite promoted expression of deleterious expansions by targeting expanded CTG DNA as well as methods using such compositions for use in treating or ameliorating the effects of a medical condition involving trinucleotide repeats in a subject. In embodiments, the present disclosure provides a method for treating a medical condition involving trinucleotide repeats, including a disease such as DM1, in a subject in need thereof by administering to the subject an effective amount of a modified polycyclic compound of the present disclosure. Processes for synthesizing modified polycyclic compounds that rescue mis-splicing at low nanomolar concentration with negligible toxicity are also disclosed.

7 Claims, 27 Drawing Sheets

(2 of 27 Drawing Sheet(s) Filed in Color)

HM19A

HM19B

HM19A (R = H) HM19B (R = ) HM42 (R = )

HM42

HM43 (R=alkyl)

DB829

HM19B

HM19A

HM33

HM42

HM43

HM31B

HM31A

HM37B

HM37E

HM35F

HM35B

HM35G

HM21A

HM35D

HM35C

HM24A

HM35I

HM35H

HM33

HM19B

COMPOSITIONS AND METHODS FOR TREATING DISEASES, DISORDERS AND CONDITIONS INVOLVING TRINUCLEOTIDE REPEATS

CROSS REFERENCE TO RELATED APPLICATIONS

This application claims the benefit of the filing date of U.S. Provisional Application No. 63/252,101 filed Oct. 4, 2021. The content of this earlier filed application is hereby incorporated by reference herein in its entirety.

STATEMENT REGARDING FEDERALLY SPONSORED RESEARCH OR DEVELOPMENT

This invention was made with governmental support under grant no. NS120485 awarded by The National Institutes of Health. The government has certain rights in this invention.

FIELD OF THE INVENTION

The present disclosure is generally in the fields of organic chemistry and medicine. More particularly, it concerns therapeutic and preventative agents for treating or preventing diseases, disorders and conditions involving trinucleotide repeats. In embodiments, the disclosure relates to identifying therapeutic and preventative agents for treating diseases, disorders and conditions involving trinucleotide repeats.

BACKGROUND

Microsatellite expansions cause over 40 neuromuscular, neurodegenerative, and neurological diseases, including Huntington's disease (HD), C9orf72 amyotrophic lateral sclerosis/frontotemporal dementia (C9-ALS/FTD) and myotonic dystrophy (DM). DM is the most common cause of muscular dystrophy with a prevalence that can vary widely depending upon the country or region.

A recent study from many samples in New York State showed 1 in 2,100 carry a CTG expansion in the DMPK gene known to cause DM type 1. Myotonic dystrophy type 1 (DM1) and type 2 (DM2) share numerous clinical symptoms across multiple tissues, including muscle weakness, atrophy and myotonia (inability to relax muscles). Cardiac conduction defects are the leading cause of death for patients, and cognitive disabilities are often the most significant concern for patients and their families. The diversity of symptoms highlights the need for therapeutic drugs that can be delivered systemically and penetrate the blood-brain barrier. With no current effective treatments for DM, the financial burden on affected individuals, families and the health care system is calculated to be in the hundreds of millions per year in the US alone.

Both DM1 and DM2 share an RNA gain-of-function (GOF) mechanism that operates primarily via sequestration of muscleblind-like (MBNL) proteins by the toxic RNA repeats, often found in foci, a hallmark of DM. MBNL sequestration results in mis-regulation of alternative splicing and many of these mis-splicing events have been linked to specific disease phenotypes. For example, mis-splicing of chloride channel 1 pre-mRNA causes myotonia and mis-splicing of sodium channel 5A has been linked to cardiac arrhythmia. The expression of CUG RNA repeats in DM1 has also been shown to alter levels of other RNA binding proteins with downstream consequences in RNA processing. For example, CELF1 is stabilized through hyper-phosphorylation causing changes in splicing and RNA stability. Concentrations of other RNA binding proteins have also been observed to change in DM, indicating that the equilibrium of RNA binding proteins is altered by toxic RNAs. Other downstream events include toxic protein expression via repeat associated non-AUG (RAN) translation. This repeat length-dependent, process, favored by hairpin-forming RNAs, can produce proteins from all three reading frames without an ATG start codon. RAN proteins accumulate in multiple microsatellite disorders, including Fragile X ataxia tremor syndrome, C9orf72 ALS/FTD, Huntington's disease, and myotonic dystrophy. The inventors have found that therapeutic approaches targeting the production of expansion RNAs have the potential to alleviate not only downstream events, but also the underlying RNA GOF mechanisms.

Prior art of interest includes U.S. Pat. Nos. 7,432,278; 8,158,364; 9,376,421; and 9,586,844 (all of which are herein entirely incorporated by reference). However, none of the prior art reference disclose compositions or agents of the present disclosure, including agents suitable for treating, preventing, or alleviating diseases, disorders and conditions involving trinucleotide repeats.

There is a continuing need in the art for additional compounds having desirable activity against diseases, disorders and conditions involving microsatellite expansions such as trinucleotide repeats.

SUMMARY

In embodiments, the present disclosure provides therapeutic and preventative compounds or agents for treating or preventing diseases, disorders and conditions involving microsatellite expansions such as trinucleotide repeats. Non-limiting examples of diseases, disorders and conditions involving trinucleotide repeats include myotonic dystrophy (DM), muscular dystrophy, Huntington disease, spinocerebellar ataxia, and Friedreich ataxia.

In embodiments, the present disclosure includes one or more polycyclic compounds, or pharmaceutically acceptable salts or solvates thereof, including: a heterocyclic core; a benzimidazole side group; and optionally, one or more functionalized end groups, wherein the heterocyclic core includes a fused ring structure, or

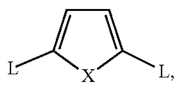

wherein L is a benzene ring, a pyrimidine ring, a pyridine ring, pyrazine ring, a pyridazine ring, or a piperazine, and wherein X is O, S, or NH. In embodiments, the one or more compounds target an expanded CTG DNA and/or inhibits microsatellite promoted expression of one or more deleterious expansions.

In embodiments, the present disclosure includes a pharmaceutical formulation, including one or more of the polycyclic compounds of the present disclosure, or pharmaceutically acceptable salts or solvates thereof, and a pharmaceutically acceptable carrier.

In embodiments, the present disclosure includes a method of treating a medical condition involving microsatellite expansion such as trinucleotide repeats in a subject in need thereof by administering to the subject an effective amount of a polycyclic compound of the present disclosure. In embodiments, the medical condition involving trinucleotide repeats is muscular dystrophy, myotonic dystrophy, Type 1 DM, Type 2 DM, or combinations thereof.

In some embodiments, the present disclosure includes a method of inhibiting microsatellite promoted expression of one or more deleterious expansions by targeting expanded CTG DNA repeats or CUG RNA repeats in a subject in need thereof by administering to the subject a therapeutically effective amount of a polycyclic compound of the present disclosure, or a pharmaceutically acceptable salt or solvate thereof.

In embodiments, the disclosure relates to identifying therapeutic and preventative agents for treating diseases, disorders and conditions involving trinucleotide repeats.

The illustrative aspects of the present disclosure are designed to solve the problems herein described and/or other problems not discussed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

Figure 1:
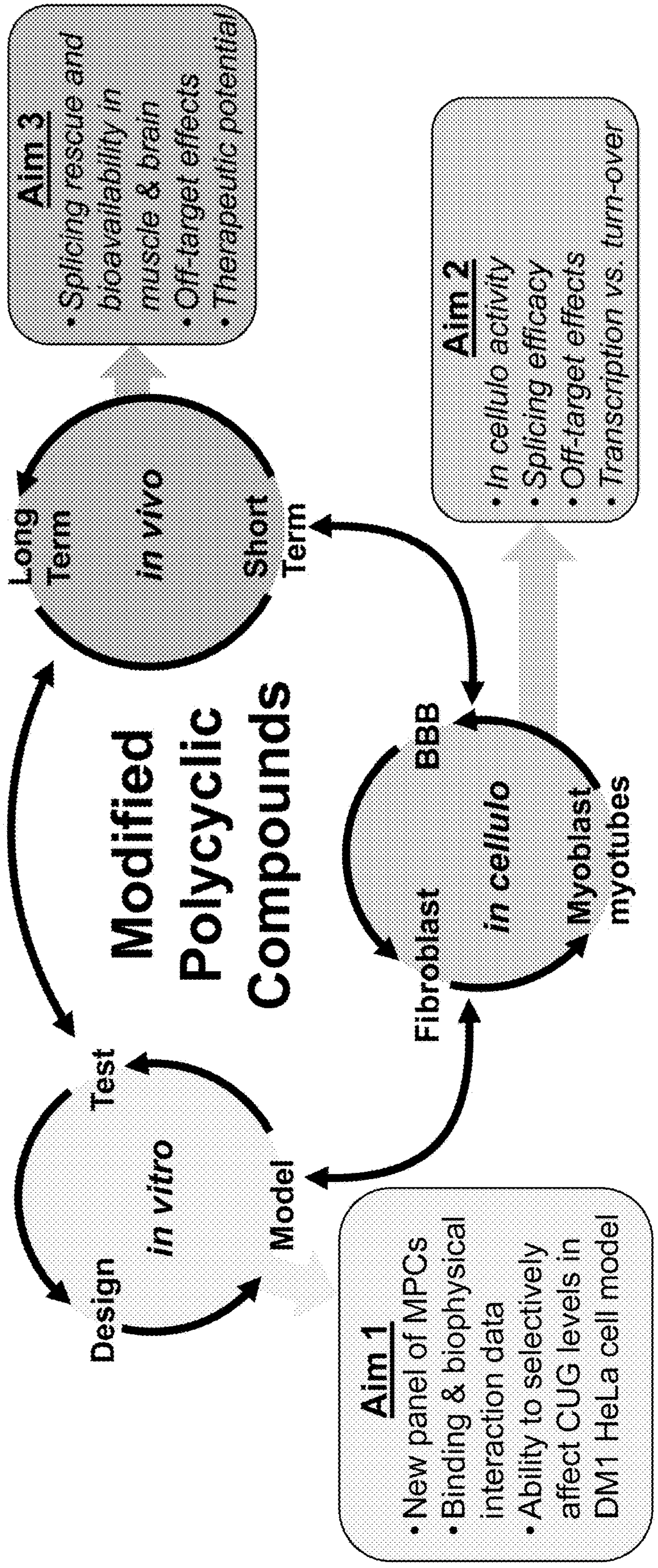
FIG. 1 depicts a schematic pipeline for the design, synthesis, and testing of polycyclic compounds of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

The presently disclosed subject matter will now be described more fully and representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Throughout the specification and claims, a given chemical formula or name shall encompass all optical and stereoisomers, as well as racemic mixtures where such isomers and mixtures exist.

The present disclosure provides therapeutic and preventative agents for treating or preventing diseases, disorders and conditions involving trinucleotide repeats. Non-limiting examples of diseases, disorders and conditions involving trinucleotide repeats include myotonic dystrophy (DM), muscular dystrophy, Huntington disease, spinocerebellar ataxia, and Friedreich ataxia fall under the group of trinucleotide repeat disorders. In embodiments, the present disclosure includes one or more polycyclic compounds, or pharmaceutically acceptable salts or solvates thereof, including: a heterocyclic core; a benzimidazole side group; and optionally, one or more functionalized end groups, wherein the heterocyclic core includes a fused ring structure, or

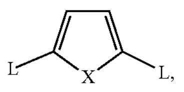

wherein L is a benzene ring, a pyrimidine ring, a pyridine ring, pyrazine ring, a pyridazine ring, or a piperazine, and wherein X is O, S, or NH. In embodiments, the one or more compounds target an expanded CTG DNA and/or inhibits microsatellite promoted expression of one or more deleterious expansions.

Advantages of the present disclosure include compositions and methods for treating, ameliorating, or preventing diseases, disorders and conditions involving microsatellite expansions and/or trinucleotide repeats. In embodiments, compositions are provided that are pharmaceutically acceptable, and/or may cross the blood/brain barrier. In embodiments, compositions of the present disclosure target, bind, and/or selectively bind to toxic RNA or DNA. In embodiments, compositions of the present disclosure regulate repeat expansions associated with disease such as myotonic dystrophy Type 1 (DM1).

Definitions

As used in the present specification, the following words and phrases are generally intended to have the meanings as set forth below, except to the extent that the context in which they are used indicates otherwise.

As used herein, the singular forms “a”, “an”, and “the” include plural references unless the context clearly dictates otherwise. Thus, for example, references to “a compound” include the use of one or more compound(s). “A step” of a method means at least one step, and it could be one, two, three, four, five or even more method steps.

As used herein the terms "about," "approximately," and the like, when used in connection with a numerical variable, generally refers to the value of the variable and to all values of the variable that are within the experimental error (e.g., within the 95% confidence interval [CI 95%] for the mean) or within ±10% of the indicated value, whichever is greater.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers to $C_{1-8}$ straight-chain alkyls. In other embodiments, "alkyl" refers to $C_{1-8}$ branched-chain alkyls. In embodiments, alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl. Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

As used herein, the term "heteroalkyl" by itself or in combination with another term means, unless otherwise stated, a stable straight or branched chain alkyl group consisting of the stated number of carbon atoms and one or two heteroatoms of 0, N, and S, and wherein the nitrogen and sulfur atoms may be optionally oxidized and the nitrogen heteroatom may be optionally quaternized. In embodiments, the heteroatom(s) may be placed at any position of the heteroalkyl group, including between the rest of the heteroalkyl group and the fragment to which it is attached, as well as attached to the most distal carbon atom in the heteroalkyl group. Non-limiting examples include: $-O-CH_2-CH_2-CH_3$, $-CH_2-CH_2-CH_2-OH$, $-CH_2-CH_2CH_2-NH-CH_3$, and $-CH_2-S-CH_2-CH_3$. In embodiments, up to two heteroatoms may be consecutive, such as, for example, $-CH_2-NH-OCH_3$, or $-CH_2-CH_2-S-S-CH_3$. In embodiments, heteroalkyl groups have 1-12 carbons.

As used herein, the term "alkenyl," denotes a monovalent group derived from a hydrocarbon moiety containing at least two carbon atoms and at least one carbon-carbon double bond. In embodiments, the double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. In embodiments, a cycloalkyl group can be optionally partially unsaturated. In embodiments, the cycloalkyl group also can be optionally substituted with an alkyl group substituent as defined herein, oxo, and/or alkylene. In embodiments, there can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Non-limiting examples of monocyclic cycloalkyl rings include cyclopentyl, cyclohexyl, and cycloheptyl. Non-limiting examples of multicyclic cycloalkyl rings include adamantyl, octahydronaphthyl, decalin, camphor, camphane, and noradamantyl.

As used herein, the term "heterocycloalkyl" or "heterocyclyl" refers to a heteroalicyclic group including one to four ring heteroatoms each selected from 0, S, and N. In embodiments, each heterocyclyl group has from 3 to 10 atoms in its ring system, with the proviso that the ring of said group does not contain two adjacent O or S atoms. In embodiments, heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. In embodiments, the heterocyclyl group has less than three heteroatoms. In embodiments, the heterocyclyl group has one to two heteroatoms. In embodiments, the heterocycloalkyl group is fused with an aromatic ring. In embodiments, nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

As used herein, the term "aromatic" refers to a carbocycle or heterocycle with one or more polyunsaturated rings and having aromatic character, i.e., having (4n+2) delocalized $\pi$ (pi) electrons, where n is an integer.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. In embodiments, the term "aryl" specifically encompasses heterocyclic aromatic compounds. The aromatic ring(s) can include phenyl, naphthyl, biphenyl, diphenylether, diphenylamine and benzophenone, among others. In particular embodiments, the term "aryl" means a cyclic aromatic including about 5 to about 10 carbon atoms, e.g., 5, 6, 7, 8, 9, or 10 carbon atoms, and including 5- and 6-membered hydrocarbon and heterocyclic aromatic rings. In embodiments, an aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl. Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Non-limiting examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

As generally discussed herein, a structure represented generally by the formula:

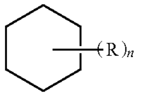

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, including a substituent R group. In embodiments, the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

 ; 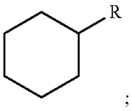 ; 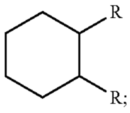 ; 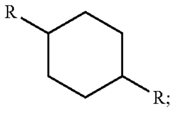 ;

and the like.

In embodiments, a dashed line representing a bond in a cyclic ring structure indicates that the bond can be either present or absent in the ring. That is a dashed line representing a bond in a cyclic ring structure indicates that the ring structure is one of a saturated ring structure, a partially saturated ring structure, and an unsaturated ring structure.

In some embodiments, the compounds described by the presently disclosed subject matter contain a linking group. As used herein, the term "linking group" includes a chemical moity, such as a furanyl, phenylene, thienyl, and pyrrolyl radical, which is bonded to two or more other chemical moieties, in particular aryl groups, to form a stable structure.

In embodiments, a named "R", or "L," group will generally have the structure that is recognized in the art as corresponding to a group having that name, unless specified otherwise herein. For the purposes of illustration, certain representative "R," "L" groups as set forth above are defined below. These definitions are intended to supplement and illustrate, not preclude, the definitions that would be apparent to one of ordinary skill in the art upon review of the present disclosure.

The terms "deoxyribonucleotide" and "DNA" refer to a nucleotide or polynucleotide including at least one ribosyl moiety that has an H at the 2' position of a ribosyl moiety. In embodiments, a deoxyribonucleotide is a nucleotide having an H at its 2' position.

As used herein, the term "transcription" refers to a process of constructing a messenger RNA molecule using a DNA molecule as a template with resulting transfer of genetic information to the messenger RNA.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, or amelioration of one or more symptoms associated with a disease or condition such as a disease or condition relating to microsatellite expansion.

As used herein, the term "target protein" refers to a molecule or a portion of a protein capable of being bound by a selective binding compound.

As used herein, the term "target RNA" refers to a molecule or a portion of an RNA capable of being bound by a selective binding compound.

As used herein, the term "target DNA" refers to a molecule or a portion of a DNA capable of being bound by a selective binding compound.

As used herein, the term "treatment" or "treating" is defined as the application or administration of a therapeutic agent, i.e., a one or more polycyclic compounds of the present disclosure, or pharmaceutically acceptable salts or solvates thereof, (alone or in combination with another pharmaceutical agent), to a patient, or application or administration of a therapeutic agent.

A "therapeutically effective amount" is that amount that will generate the desired therapeutic outcome (i.e., achieve therapeutic efficacy). For example, a therapeutically effective dose of a compound of the present disclosure is an amount that is sufficient to palliate, ameliorate, stabilize, reverse, prevent, slow or delay the progression of the disease state (e.g., DM1). A therapeutically effective amount can be an amount administered in a dosage protocol that includes days or weeks of administration. In certain embodiments, a therapeutically effective dose of a compound is able to improve at least one sign or symptom of a disease state. As used herein, the terms "effective amount," and "pharmaceutically effective amount," have the same meaning as "therapeutically effective amount". In embodiments, a therapeutically effective amount alters the natural state of a subject.

As used herein, the term "patient," "individual" or "subject" refers to a human or a non-human mammal. Non-human mammals include, for example, livestock and pets, such as ovine, bovine, porcine, canine, feline and murine mammals. Non-human mammals also include non-human primates, rats, rabbits and camelids. In certain embodiments, the patient, subject, or individual is human.

As used herein, the phrases "selective inhibition" or "selectively inhibit" refer to a molecule's ability to inhibit the activity or expression of a particular protein or protein isoform, or RNA, while being unable to inhibit the protein activity or expression of another protein or protein isoform, or RNA, by more than 5%.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of one or more of the polycyclic compounds of the present disclosure, wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "solvate" refers to complexes of the compounds disclosed herein or salts thereof with solvent molecules, e.g. organic solvent molecules and/or water.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. In embodiments, there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gaited., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Before embodiments are further described, it is to be understood that this disclosure is not limited to particular embodiments described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

DESCRIPTION OF CERTAIN EMBODIMENTS

In embodiments, the present disclosure includes one or more polycyclic compounds, or pharmaceutically acceptable salts or solvates thereof, including: a heterocyclic core; a benzimidazole side group; and optionally, one or more functionalized end groups, wherein the heterocyclic core includes a fused ring structure, or

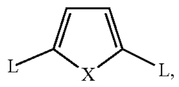

wherein L is a benzene ring, a pyrimidine ring, a pyridine ring, pyrazine ring, a pyridazine ring, or a piperazine, and wherein X is O, S, or NH. In embodiments, the heterocyclic core, incudes a furane, dibenzopyrrole, or dibenzofuran. In embodiments, one or more compounds of the present disclosure targets or selectively targets an expanded CTG DNA, CUG RNA, and/or inhibits or selectively inhibits microsatellite promoted expression of one or more deleterious expansions. In embodiments, the benzimidazole side group includes a benzimidazoline including a benzene ring fused with an imidazoline. In embodiments, the one or more functionalized end groups include one or more of methylpiperazine, n-methylpiperazine, or a carboxyl group (C(=O)OH)). In embodiments, one or more compounds of the present disclosure are pharmaceutically acceptable and/or suitable for rescue mis-splicing at low nanomolar concentration with negligible toxicity.

In embodiments, a polycyclic compound of the present disclosure is

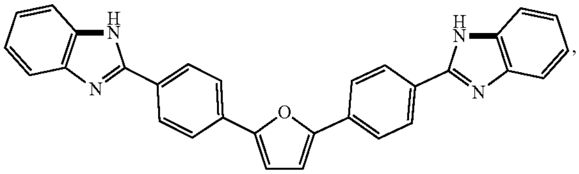

or a pharmaceutically acceptable salt or solvate form thereof.

In embodiments, a polycyclic compound of the present disclosure is

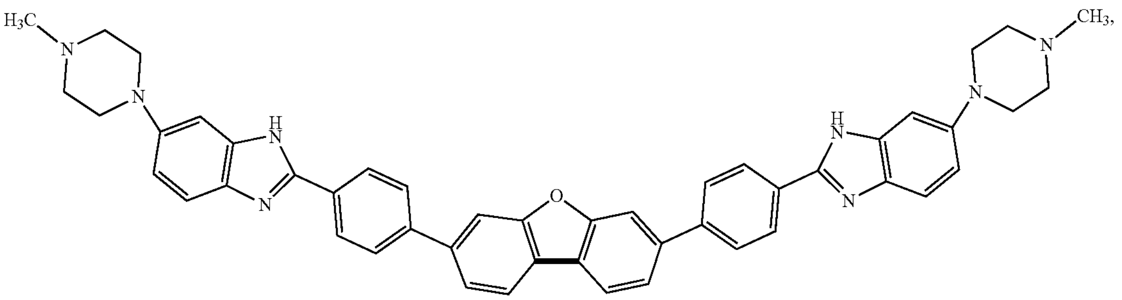

or a pharmaceutically acceptable salt or solvate thereof.

In embodiments, a polycyclic compound of the present disclosure is

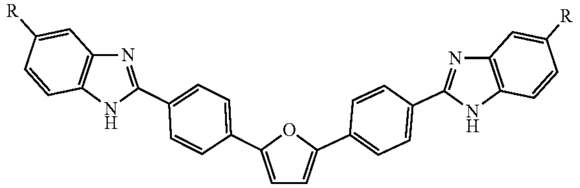

or a pharmaceutically acceptable salt or solvate thereof, wherein R is H, alkyl, a carboxyl group (C(═O)OH)), or n-methylpiperazine, or combinations thereof. In embodiments, one or more benzene rings are replaced with one or more pyridine rings. For example, a first benzene ring or a second benzene ring linked by a furane may be substituted or replaced with one or more pyridine rings.

In embodiments, a polycyclic compound of the present disclosure is characterized as having a formula of:

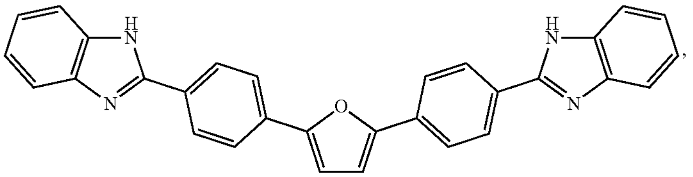

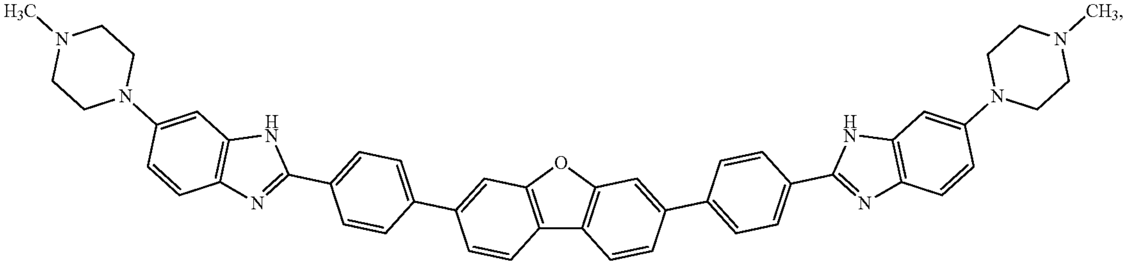

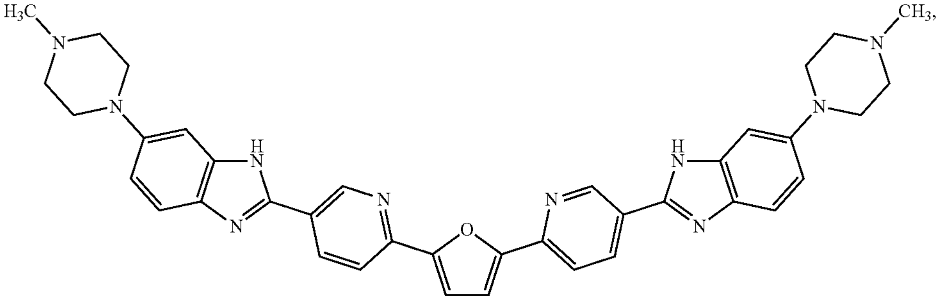

-continued
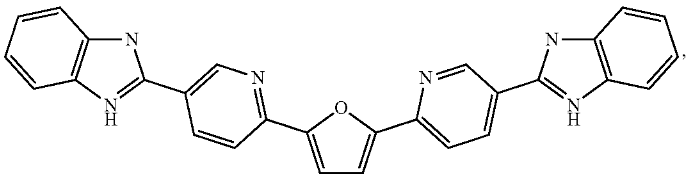,
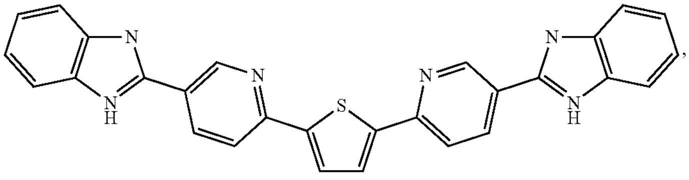,
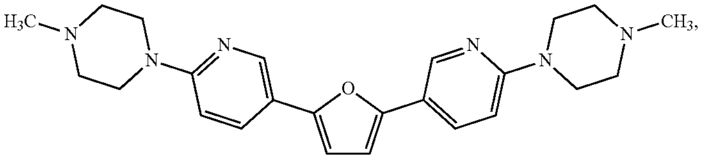,
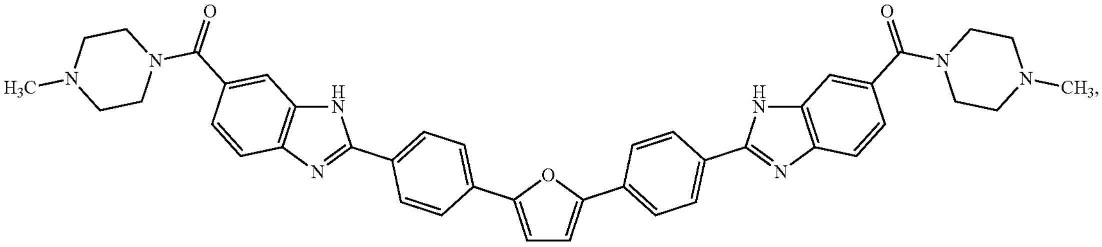,
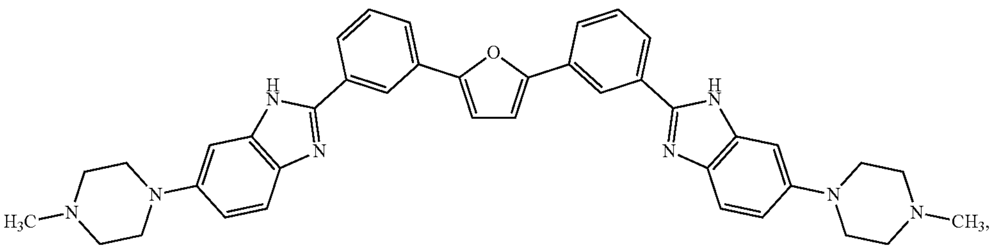, or
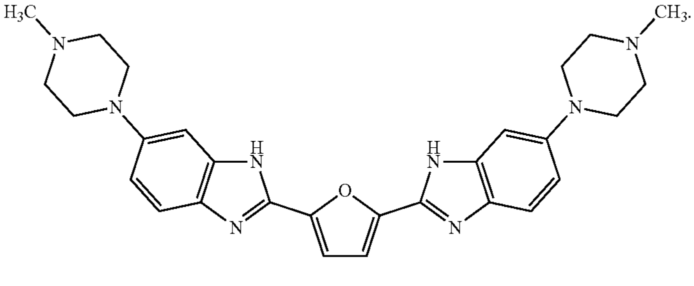

In embodiments, a polycyclic compound of the present disclosure is characterized as having a heterocyclic core including a fused ring structure, such as those compounds or agents represented by one or more formulas as shown below:
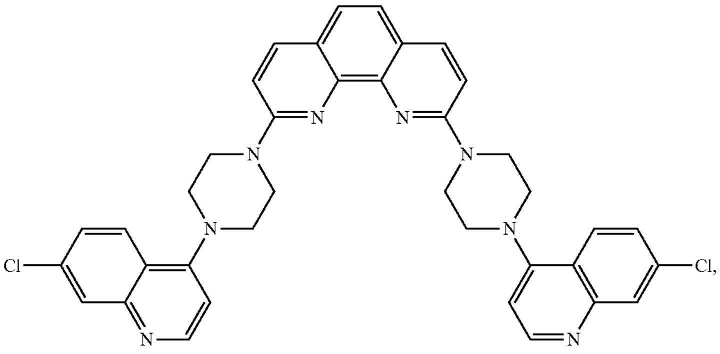
,
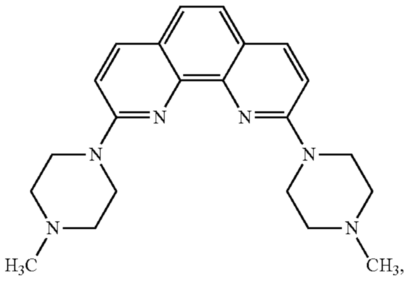
,
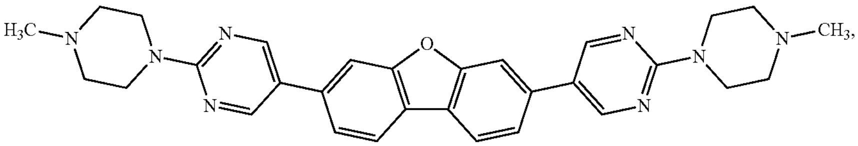
,
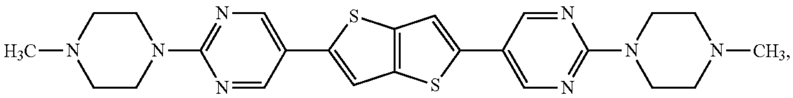
,
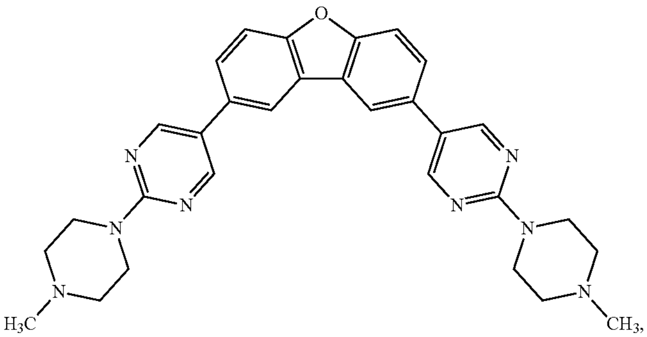
,
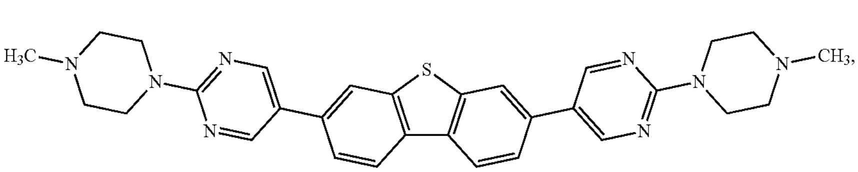
,
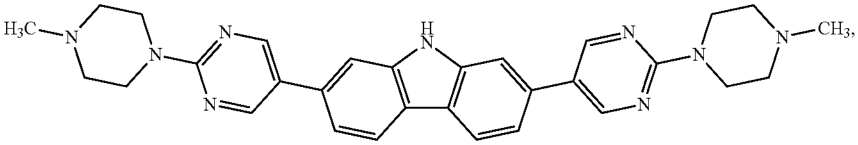
, -continued

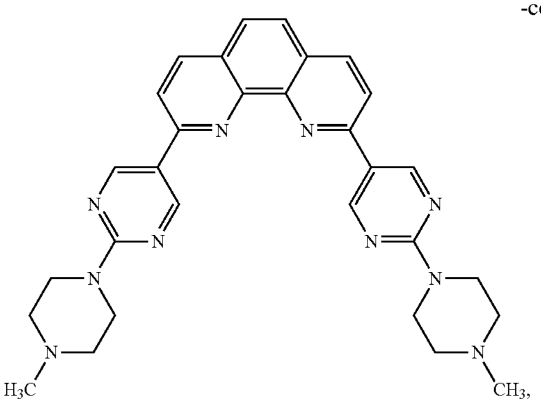

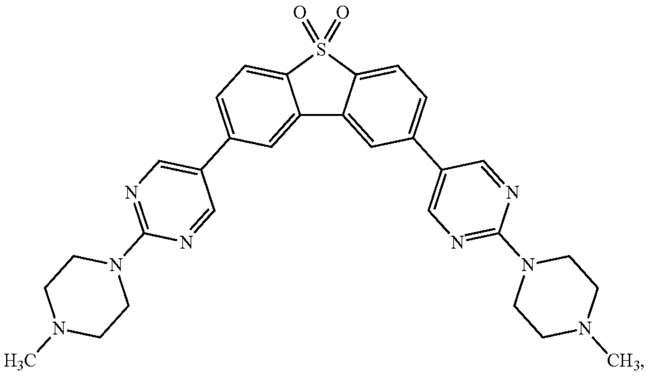

or

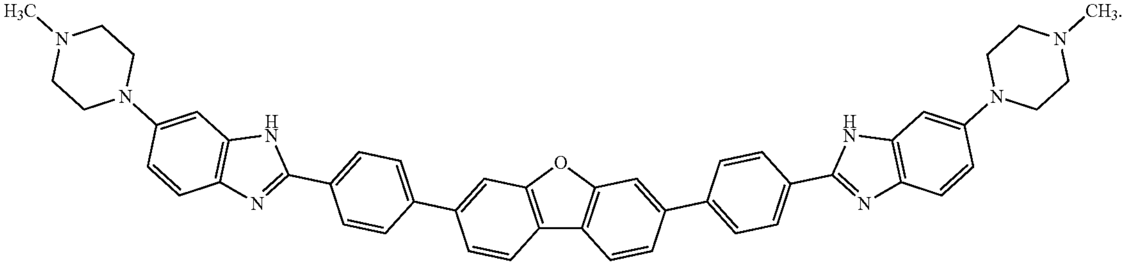

In embodiments, the present disclosure includes compounds of Formula I as shown below:

(I)

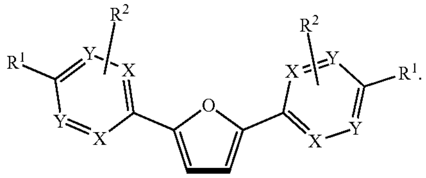

In embodiments, X═Y. In embodiments X═Y═N. In embodiments, X is CH. In embodiments, $R^1$ is cyclohexyl having heroatoms 2-4 selected from N, or optionally substituted with alkyl, higher alkyl, lower alkyl, or optionally substituted with carbonyl amides. In embodiments, $R^2$ is alkyl, higher alkyl, lower alkyl, electron withdrawing, or electron donating.

In embodiments, the present disclosure includes compounds of Formula II as shown below:

(II)

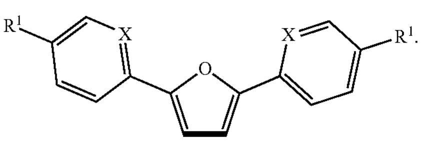

In embodiments, X═N, CH; $R^1$ is aryl, heteroaryl having 2 heteroatoms selected from N and optionally substituted with cyclohexyl having heteroatoms selected from N and substituted with alkyl, further optionally substituted with a carbonyl amide.

In embodiments, one or more compounds or formulas as disclosure herein is provided as a pharmaceutically acceptable salt such as derivatives of one or more of the polycyclic compounds of the present disclosure. In embodiments, a parent compound such as a polycyclic compound of the present disclosure is modified by converting an existing acid or base moiety thereof to a salt form. Examples of pharmaceutically acceptable salts include, but are not limited to, mineral or organic acid salts of basic residues such as amines; alkali or organic salts of acidic residues such as carboxylic acids; and the like. In embodiments, the pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile.

In embodiments, the polycyclic compounds of the present disclosure may possess one or more stereocenters, and each stereocenter may exist independently in either the R or S configuration.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

In embodiments, the polycyclic compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Non-limiting examples of isotopes suitable for inclusion in the compounds described herein include and are not limited to $^2H$ or deuterium. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In embodiments, the compounds described herein are labeled by other means, including, but not limited to, the use of chromophores or fluorescent moieties, bioluminescent labels, or chemiluminescent labels.

In embodiments, the compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources or are prepared using procedures described herein.

In embodiments, compounds of the present disclosure, such as compounds of Formula I above or (c) below, can be synthesized using Suzuki coupling chemical reaction or according to the following scheme:

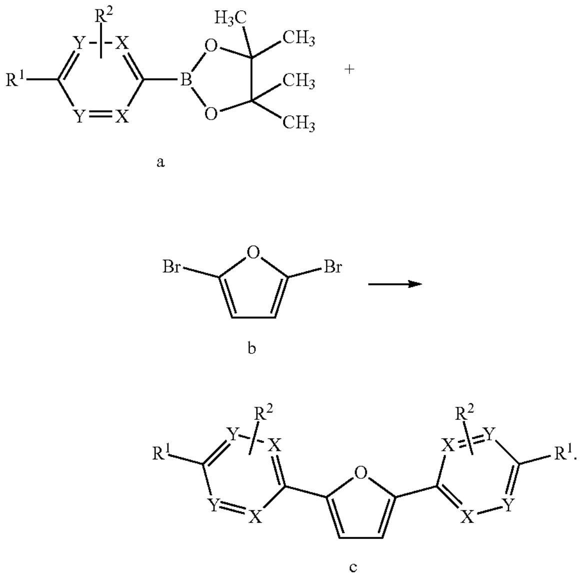
a
b
c

R1 = R1; R2 = R2; X = Y = CH, N

In embodiments, compounds of the present disclosure, such as compounds of Formula II above or below, can be synthesized using standard Suzuki coupling chemical reaction, followed by condensation with diamine. Derivatization of amines by standard amide-based reaction using carbodiimide chemistry with the use of reagents like HATU is suitable for use herein. In embodiments, compounds can be made according to the following scheme:

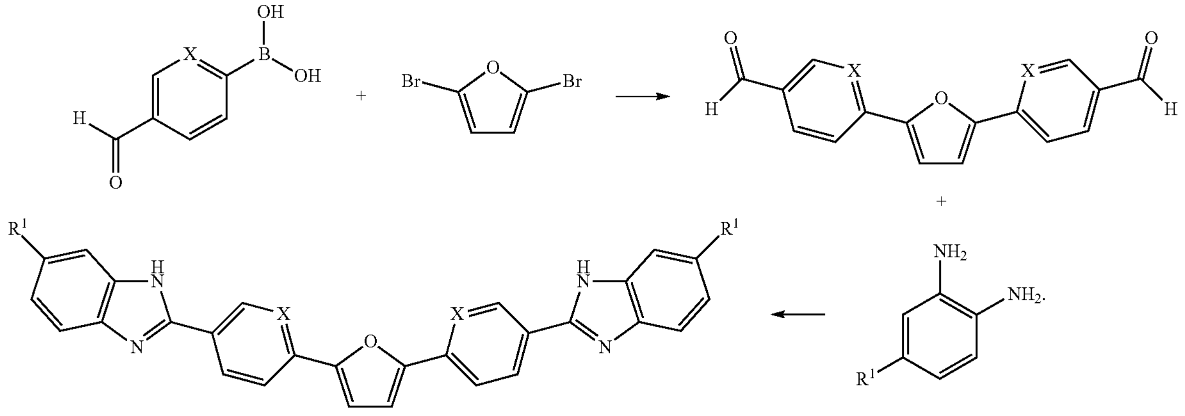

X = X = CH, N; R1 = R1 = carbonyl amides, cyclohexyl containing N

In embodiments, compounds of the present disclosure, such as compounds of Formula II above or (e) below, can be synthesized using standard Palladium catalyzed cross-coupling chemical reaction followed by condensation with diamine. Derivatization of amines by standard amide-based reaction using carbodiimide chemistry with the use of reagents like HATU is suitable for use herein. In embodiments, compounds can be made according to the following scheme:

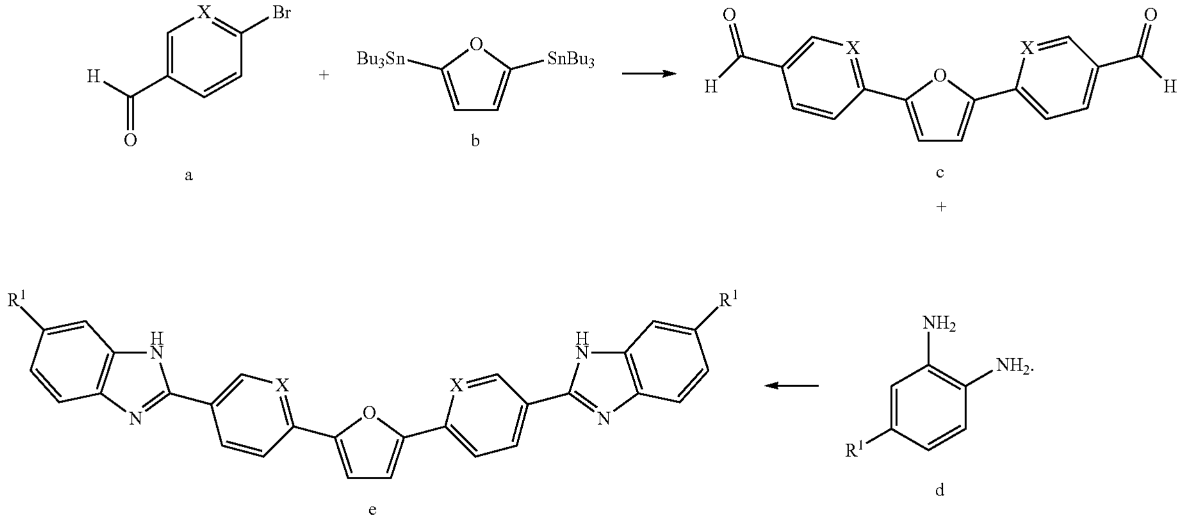

a b c d e

X = X = CH, N; R1 = R1 = carbonylamide, cyclohexyl containing N

In embodiments, the one or more polycyclic compounds, such as those sited above and below or pharmaceutically acceptable salts or solvates thereof of the present disclosure are suitable for use in treating, ameliorating, or preventing diseases, disorders and conditions involving microsatellite expansions and/or trinucleotide repeats. In embodiments, compositions are provided that are pharmaceutically acceptable, and/or may cross the blood/brain barrier. In embodiments, compositions of the present disclosure target, bind, and/or selectively bind to toxic RNA to minimize, alleviate or end downstream deleterious aspects associated therewith. In embodiments, compositions of the present disclosure regulate repeat expansions associated with disease such as myotonic dystrophy Type 1 (DM1). Non-limiting examples of diseases, disorders and conditions involving microsatellite expansion and trinucleotide repeats include myotonic dystrophy (DM), muscular dystrophy, Huntington disease, spinocerebellar ataxia, and Friedreich ataxia. In embodiments, inhibition is obtained by targeting an expanded CTG DNA, CUG RNA, and/or microsatellite promoted expression of one or more deleterious expansions. In embodiments, selective inhibition in healthy cells leads to effective reduction in expanded CTG DNA, CUG RNA, and/or microsatellite promoted expression of one or more deleterious expansions.

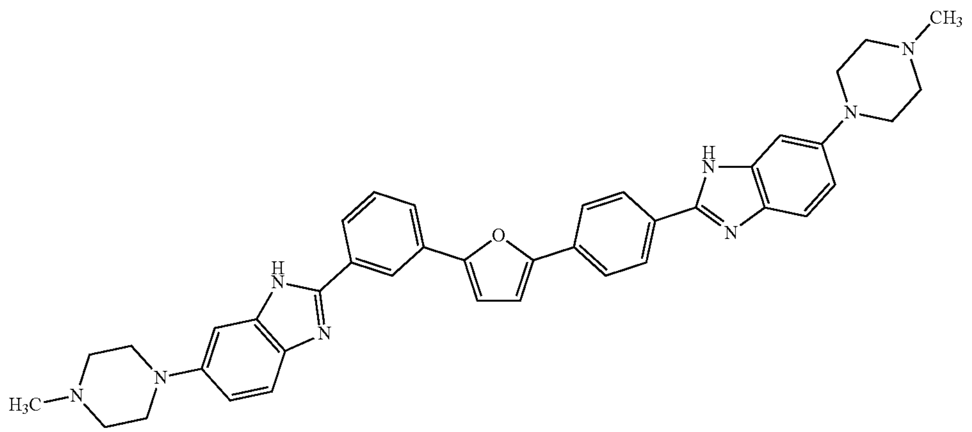
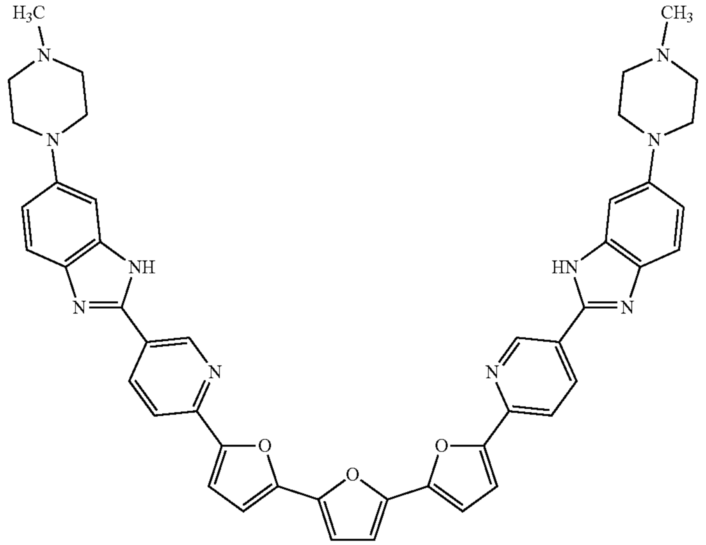
HM-061
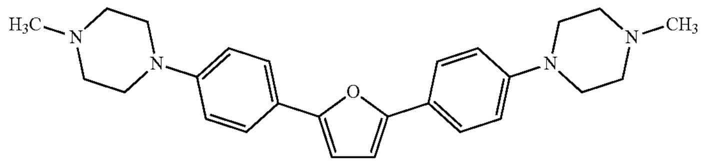
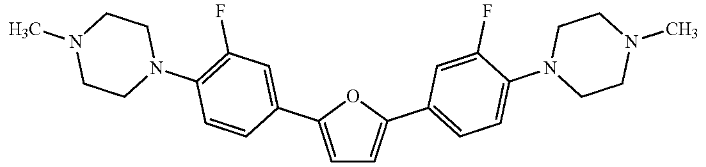
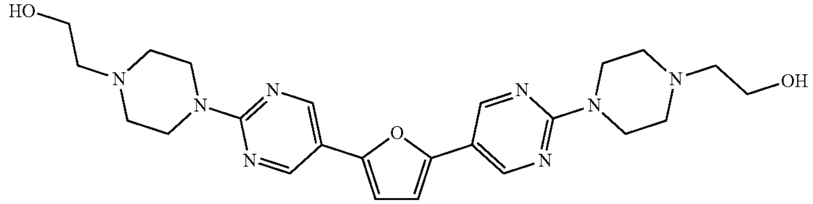
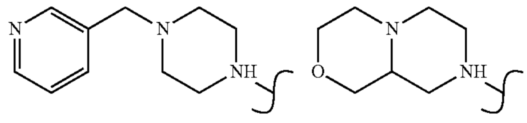
R =
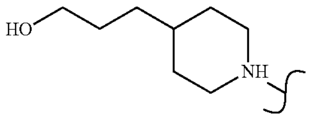

-continued
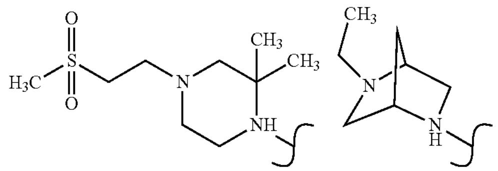
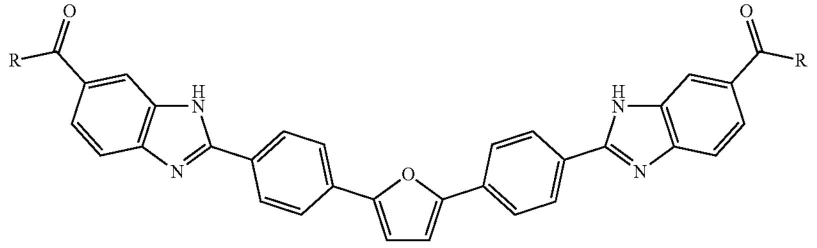
HM-043
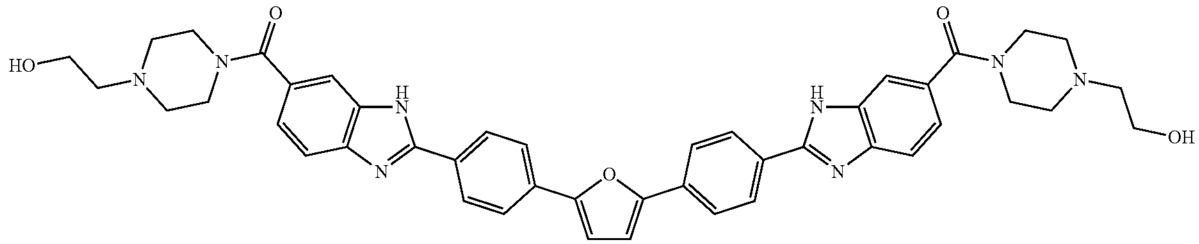
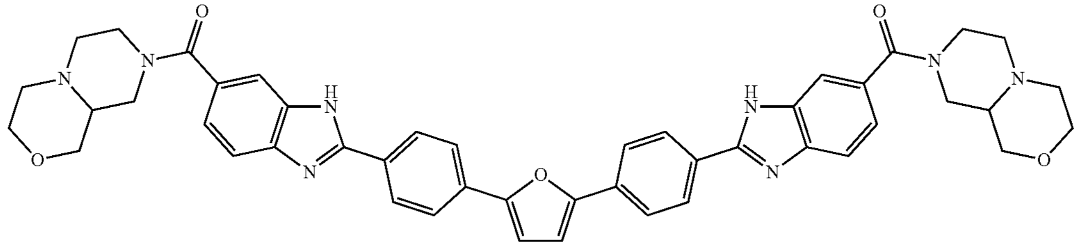
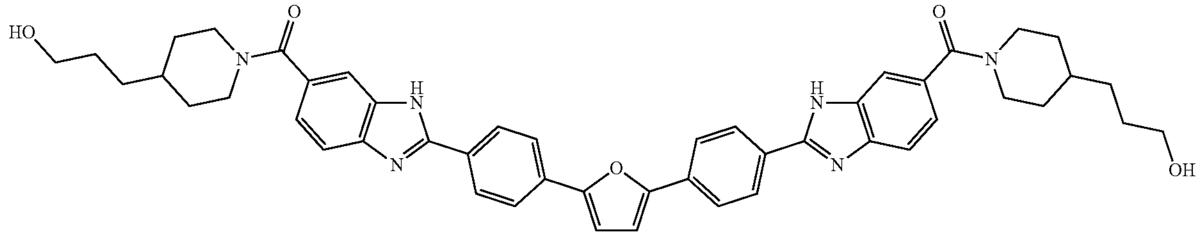
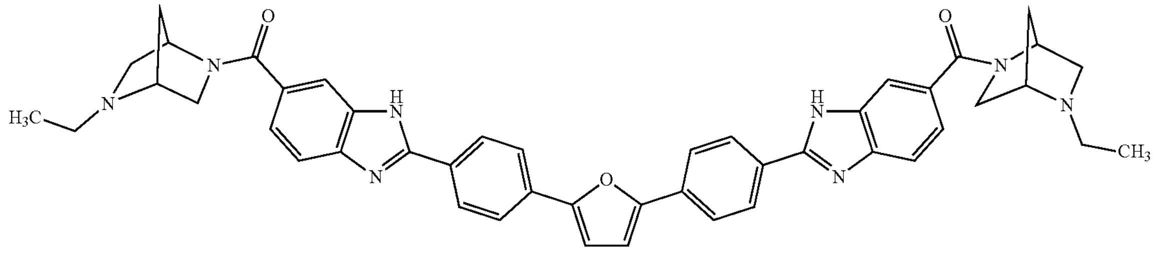
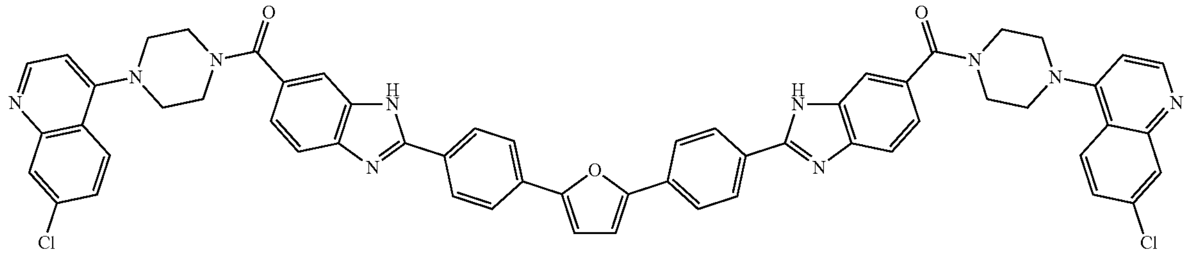

-continued

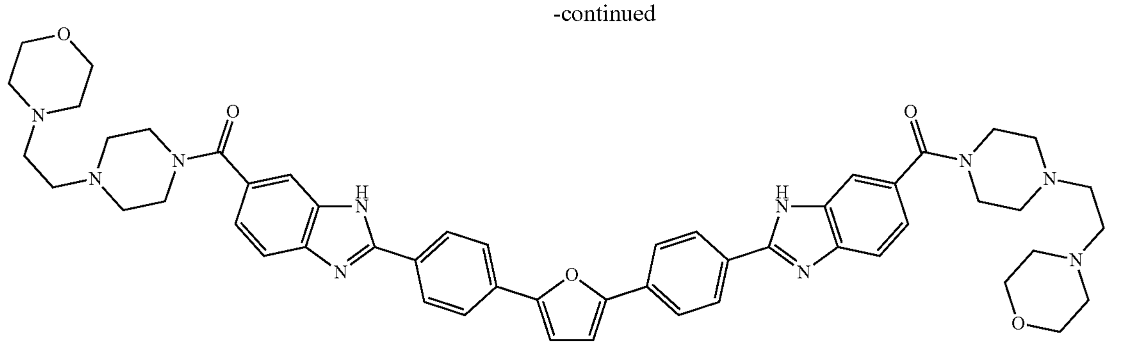

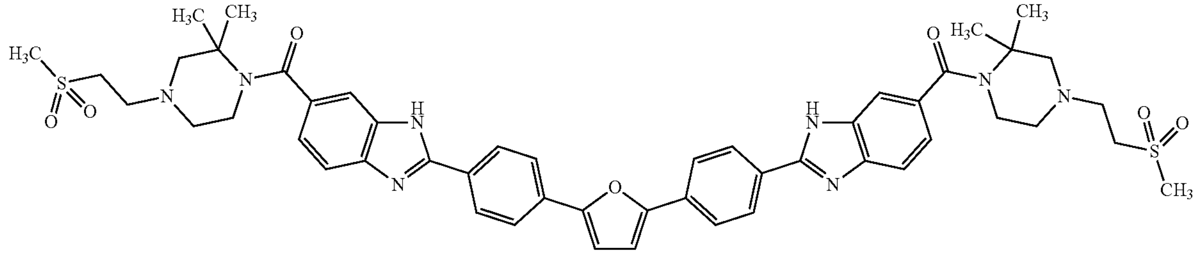

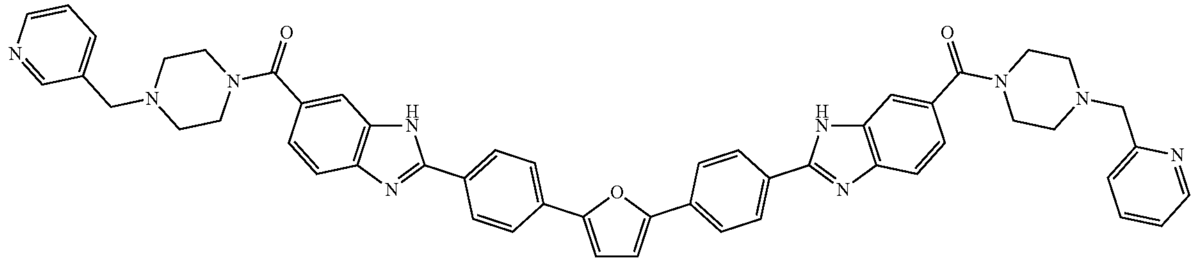

Provided herein are methods of treating a medical condition involving trinucleotide repeats in a subject in need thereof by administering to the subject an effective amount of a polycyclic compound of the present disclosure such as those identified above in Formula I and II. In embodiments, the medical condition involving trinucleotide repeats is muscular dystrophy, myotonic dystrophy, Type 1 DM, Type 2 DM, or combinations thereof. In some embodiments, the effective amount is an amount sufficient to block one or more harmful effects of an expanded DNA in a DMPK gene (type 1) or a ZNF9 gene (type 2). In embodiments, pharmaceutical agents of the present disclosure are provided in a therapeutically acceptable amount, in a form characterized as pharmaceutically acceptable.

In embodiments, the present disclosure includes a method of inhibiting microsatellite promoted expression of one or more deleterious expansions by targeting expanded CTG DNA repeats in a subject in need thereof by administering to the subject a therapeutically effective amount of a polycyclic compound of the present disclosure such as Formula I and Formula II shown above, or a pharmaceutically acceptable salt or solvate thereof.

Figure 5A:
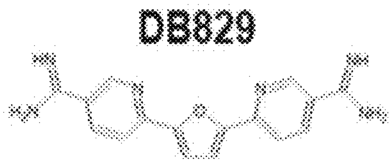
FIGS. 5A-5B depict modified polycyclic compounds of the present disclosure.
Figure 5A:
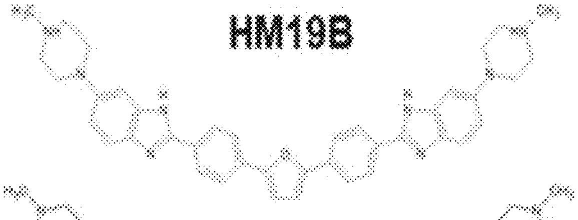
Figure 5A:
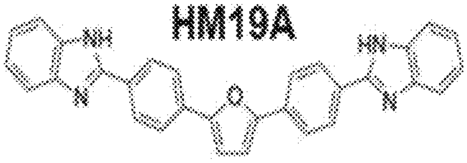
Figure 5A:
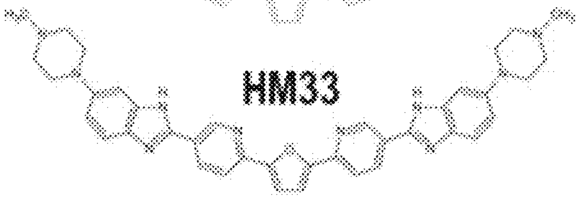
Figure 5A:
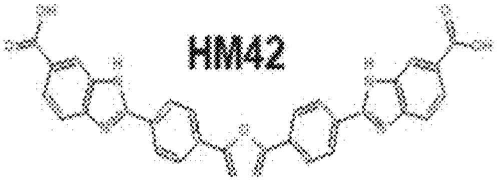
Figure 5A:
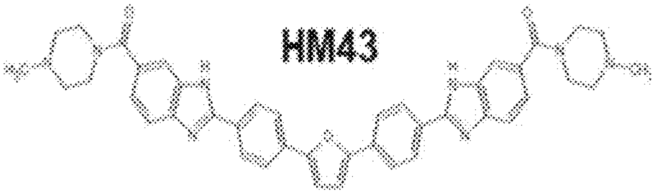
Figure 5A:
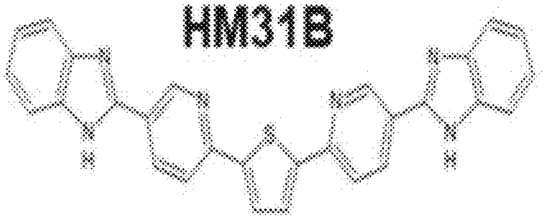
Figure 5A:
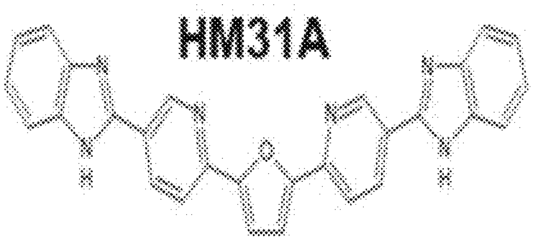
Figure 5A:
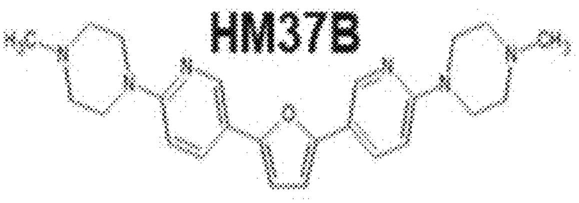
Figure 5A:
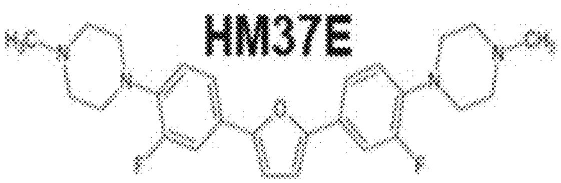
Figure 5B:
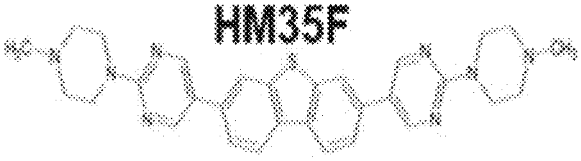
Figure 5B:
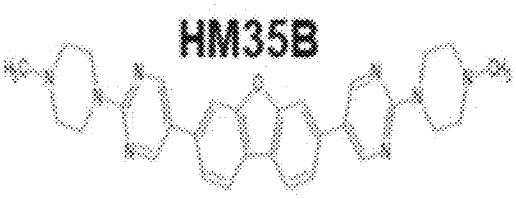
Figure 5B:
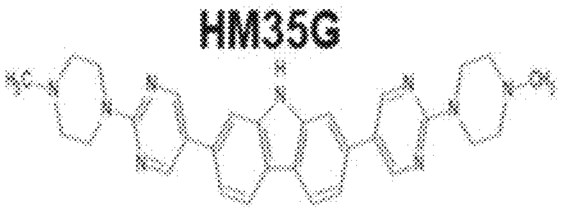
Figure 5B:
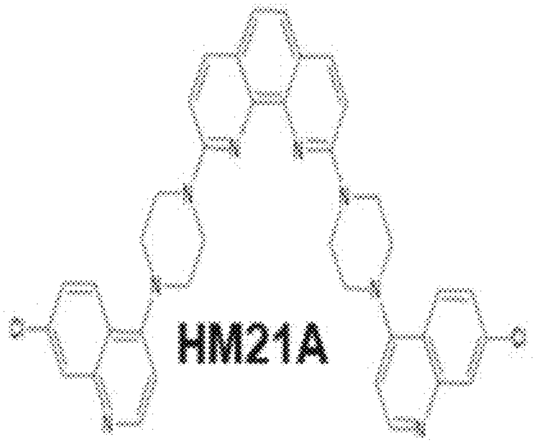
Figure 5B:
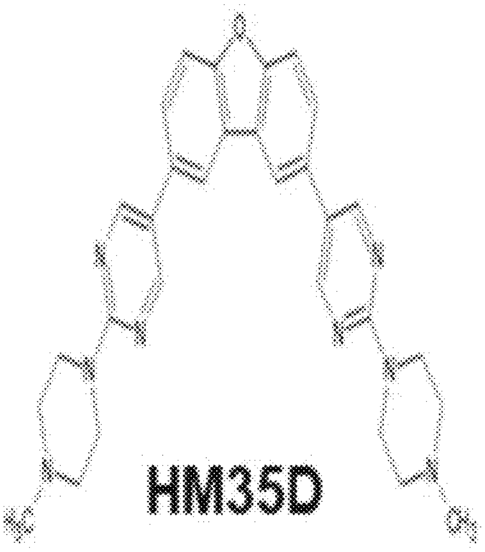
Figure 5B:
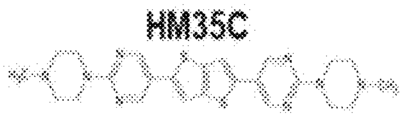
Figure 5B:
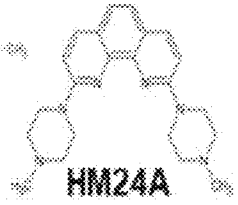
Figure 5B:
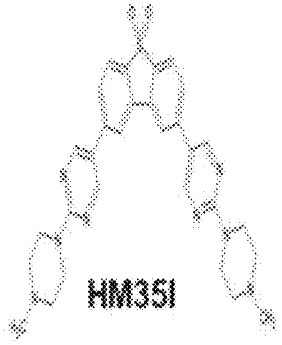
Figure 5B:
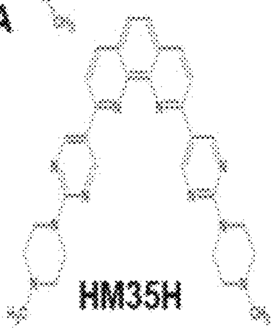

In embodiments, the compositions of the present disclosure are suitable for use in a pharmaceutically acceptable formulation. In embodiments, the present disclosure includes a pharmaceutical formulation including a polycyclic compound of the present disclosure such as Formula I and Formula II shown above, or a pharmaceutically acceptable salt, and a pharmaceutically acceptable carrier. In embodiments, a polycyclic compound of the present disclosure such as Formula I and Formula II shown, or as shown in FIGS. 5A and 5B may be referred to as an active compound. Pharmaceutical formulations including the active compounds also are provided herein. These pharmaceutical formulations include active compounds as described herein, in a pharmaceutically acceptable carrier. Pharmaceutical formulations can be prepared for oral, intravenous, or aerosol administration. Also, the presently disclosed subject matter provides such active compounds that have been lyophilized and that can be reconstituted to form pharmaceutically acceptable formulations for administration, for example, as by intravenous or intramuscular injection. In embodiments, a therapeutically effective dosage of any specific active compound, the use of which is within the scope of embodiments described herein, will vary somewhat from compound to compound, and patient to patient, and will depend upon the condition of the patient and the route of delivery.

Administration/Dosage/Formulations

In embodiments, provided herein is a pharmaceutical composition including at least one polycyclic compound of the present disclosure such as Formula I and Formula II shown above, as shown in FIGS. 5A and/or 5B, or a pharmaceutically acceptable salt or solvate thereof. Actual dosage levels of the active ingredients in the pharmaceutical compositions of this disclosure may be varied to obtain an amount of the active ingredient that is effective to achieve the desired therapeutic response for a particular patient, composition, and mode of administration, without being toxic to the patient.

In embodiments, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the polycyclic compound of the present disclosure such as Formula I and Formula II shown above, or in FIGS. 5A and 5B, at levels lower than that required to achieve the desired therapeutic effect and gradually increase the dosage until the desired effect is achieved.

In some embodiments, the compounds and salts disclosed herein may be administered as a solvate in a continuous manner. For example, a single dose may be administered to a subject as a solvate (e.g., intravenously or a delayed release capsule) for an administration period of 1, 2, 3, 4, 5, 6, 7, 8, 9, 10, 15, 30, 45, or 60 minutes. In some embodiments, a single dose may be administered to a subject as a solvate for an administration period of 1-5, 5-10, 10-15, 15-30, 30-45, or 45-60 minutes. In some embodiments, a single dose may be administered to a subject as a solvate for an administration period of 1-60 minutes. In some embodiments a single dose may be administered to a subject for an administration period of 1, 2, 3, 4, 5, 6, 7, 8, 9, 10, 11, 12, 24, 36, 48, 60, or 72 hours. In some embodiments a single dose may be administered to a subject for an administration period of 1-6, 6-12, 12-24, 24-48, 48-60, 60-72 hours. In some embodiments a single dose may be administered to a subject for an administration period of 1-72 hours.

In some embodiments, multiple doses of the compounds and salts described herein may be administered to a subject in a pulsatile or intermittent manner. As used herein the term "pulsatile dose regimen" or "intermittent dose regimen" refers to a dose administration regimen which includes at least two dosing cycles. Each subsequent dosing cycle is separated by a rest period from the preceding dosing cycle.

In particular embodiments, it is especially advantageous to formulate the compound in dosage unit form for ease of administration and uniformity of dosage. "Dosage unit form" as used herein refers to physically discrete units suited as unitary dosages for the patients to be treated; each unit containing a predetermined quantity of the polycyclic compound of the present disclosure such as Formula I and Formula II shown above calculated to produce the desired therapeutic effect in association with the required pharmaceutical vehicle. The dosage unit forms of the disclosure are dictated by and directly dependent on (a) the unique characteristics of the polycyclic compound of the present disclosure such as Formula I and Formula II shown above and the particular therapeutic effect to be achieved, and (b) the limitations inherent in the art of compounding/formulating such a polycyclic compound of the present disclosure such as Formula I and Formula II shown above, or FIGS. 5A and 5B, for treatment in a patient.

In one embodiment, the compounds of the disclosure are formulated using one or more pharmaceutically acceptable excipients or carriers. In one embodiment, the pharmaceutical compositions of the invention comprise a therapeutically effective amount of a polycyclic compound of the present disclosure such as Formula I and Formula II shown above, or FIGS. 5A and 5B, and a pharmaceutically acceptable carrier.

Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the polycyclic compound of the present disclosure such as Formula I and Formula II shown above may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present disclosure.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

Example I (Prophetic)

In embodiments, the present disclosure includes strategies and methods to address the unmet need for therapeutic approaches applied to repeat expansion diseases, such as myotonic dystrophy. The current primary therapeutic focus for toxic RNA in expansion diseases has been to develop small molecules, peptides, ribozymes, siRNAs, CRISPR and allele specific oligonucleotide (ASOs) to release (RNA-binding proteins) RBPs from repeats or degrade the toxic expansion transcripts. While ASOs are being prepared for clinical trials, currently problematically high doses are required to achieve skeletal muscle delivery and therapeutic efficacy. There remains a need to develop alternative and/or complementary therapeutic approaches for repeat expansion diseases, such as myotonic dystrophy, including compositions and therapies that work independently or in combination with an alternative approach such as ASOs. In embodiments, the present disclosure provides one or more therapeutic small molecules for repeat expansion diseases, such as myotonic dystrophy.

Low concentrations (sub-micromolar) of different classes of small molecules selectively inhibit CTG repeat transcription in DM1 cells and a DM1 mouse model. Based on this understanding the inventors target production of the toxic expansion RNA to alleviate all the known and potentially unknown pathogenic consequences in repeat expansion diseases, such as myotonic dystrophy.

In embodiments, the inventors provide a novel approach to DM treatment referred to as inhibition of microsatellite promoted expression of deleterious expansions (IMPEDE). By targeting the expanded CTG DNA, the approach of the present disclosure uses lower concentrations of small molecules compared to alternate therapies that target the expanded CUG RNA. Without wishing to be bound by the present disclosure, since there is only one target DNA molecule per cell compared to multiple RNA molecules, and hence thousands of RNA binding sites, each DNA binding event occurs in cis with other binding events. Since the production of mature mRNA requires that RNA polymerase II elongate through every single binding event, the probability of a cis interaction occurring scales exponentially with the number of binding events, as opposed to linearly, in the case of MBNL displacement from RNA. Thus, the therapeutic hurdles are much lower for IMPEDE than approaches that target the RNA alone. The present disclosure describes the generation, identification, and characterization of a new class of compounds, characterized as modified polycyclic compounds.

In embodiments, rational drug design is used to synthesize modified polycyclic compounds (MPCs) of the present disclosure such as those that rescue mis-splicing at low nanomolar concentration with negligible toxicity. For design of these small molecules, an innovative modular approach is used focusing on systematic replacement, testing and refinement of three MPC elements (core, side and end groups).

The compounds or molecules of the present disclosure are tested in innovative ways using a design-model-test approach incorporating biophysical/biochemical assays, a HeLa CTG repeat-selective screening cell line, patient-derived cell lines, blood brain barrier assays and DM mouse models (See e.g., FIG. 1 depicting methods of the present disclosure for the design, synthesis and testing of MPCs for treatment of DM in accordance with the present disclosure). In embodiments, patient-derived cell lines are characterized extensively for screening purposes with multiple small molecules enabling baseline comparisons across compounds. Additionally, in embodiments, DM1-specific, DM2-specific and shared splicing events have been identified in these cells. Thus, embodiments of the present disclosure combine screening MPCs in both DM1 and DM2 patient-derived lines with disease-specific and general splicing targets and across different classes of compounds. Compared to previous studies which focused almost exclusively on DM1, common splicing events and one class of compound, embodiments of the present disclosure provide a better understanding of disease biology and the mechanism of action of these compounds. Given the complex disease presentation of DM1, embodiments are selected to screen lead candidates in two DM1 mouse transgenic lines: (1) the well characterized muscle-specific HSALR and newer HSAXLR mouse model and (2) the newly generated endogenous Dmpk-based CTG480/480 mouse, which expresses expansion repeats in multiple tissue systems including the central nervous system (CNS). The combination of in-vitro characterization coupled to in vivo screening and animal model efficacy testing yields critical information on mechanism of action, disease biology and helps to accelerate new small molecules towards clinical testing.

Figure 9:
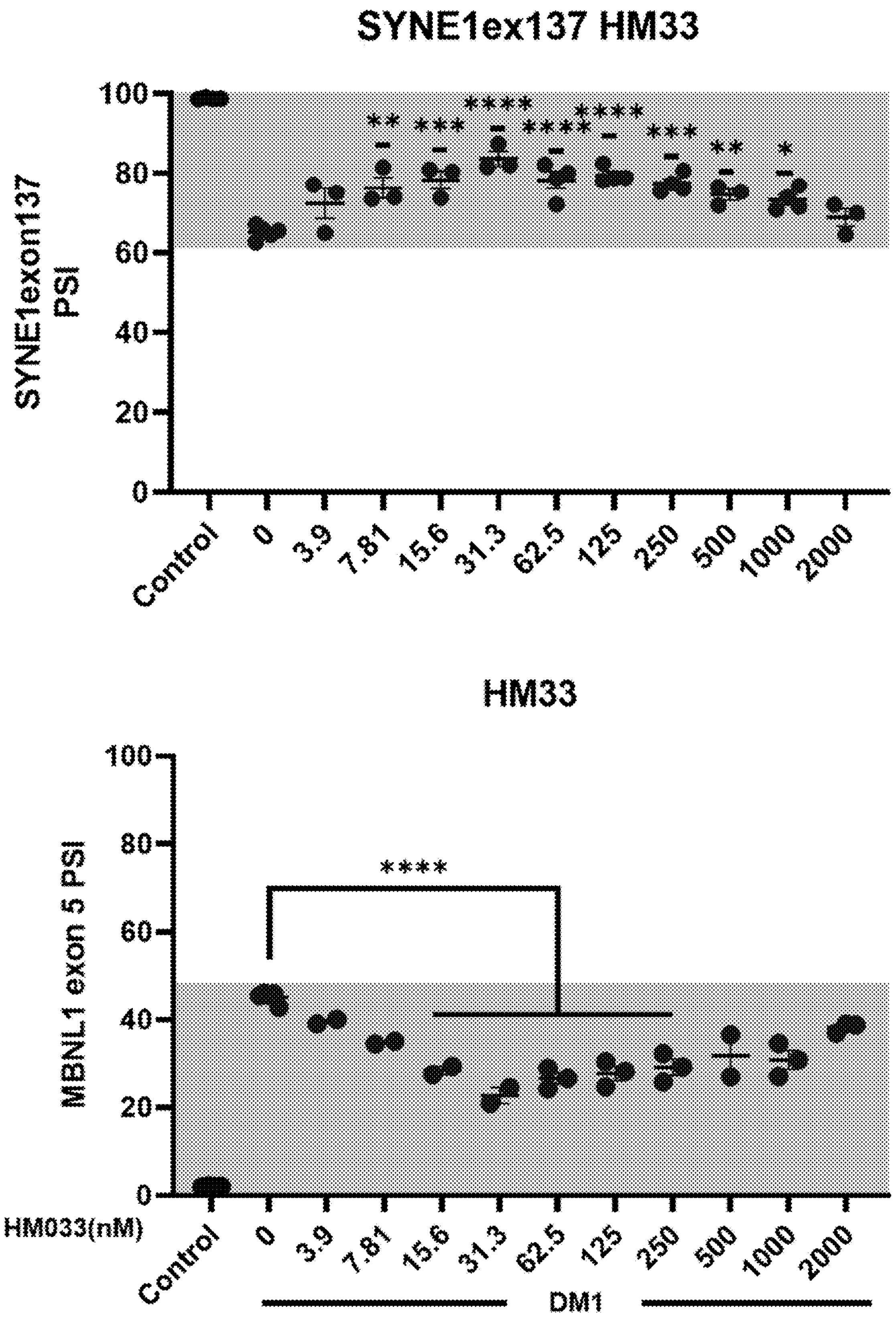
FIG. 9 presents HM33 rescues mis-splicing in DM1 myotubes with 72-hour treatment.
Figure 10:
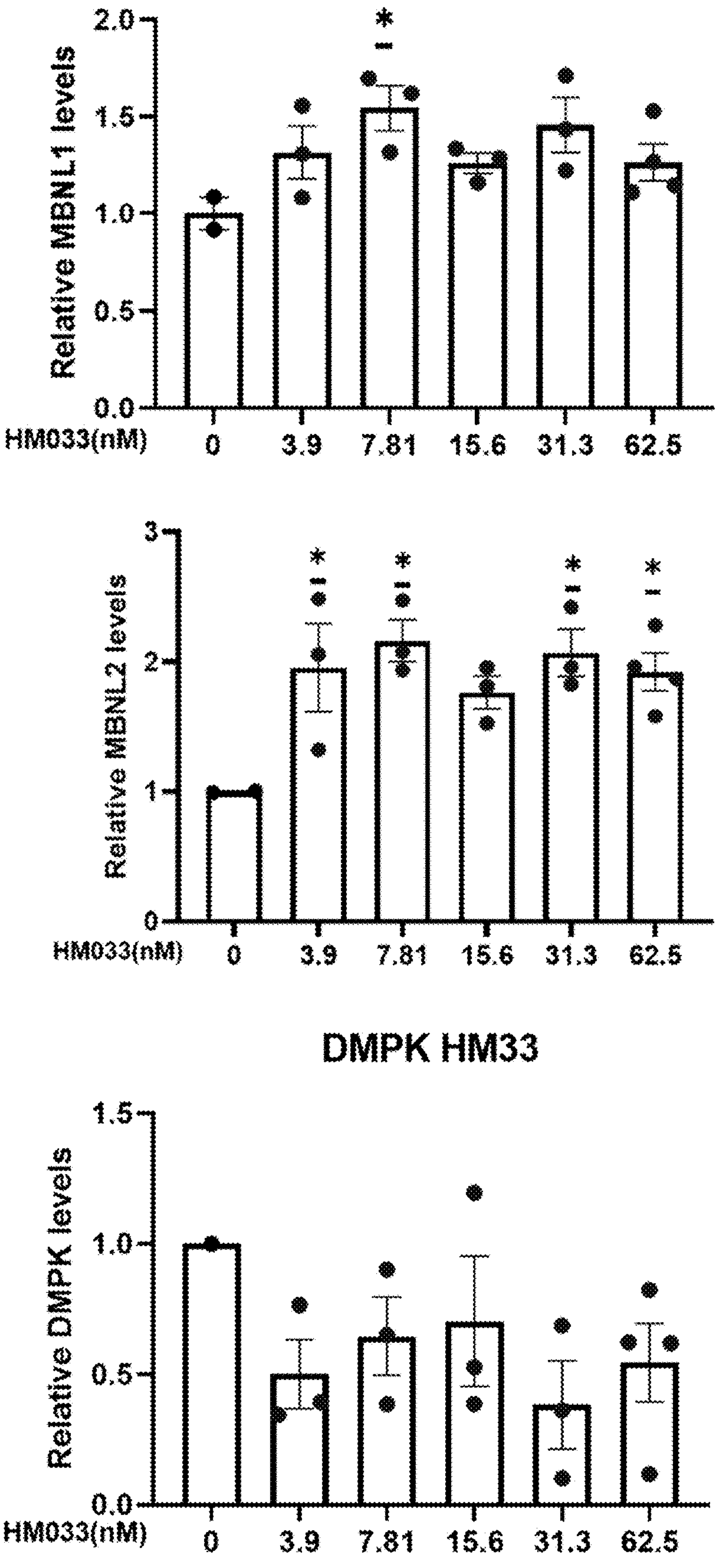
FIG. 10 presents HM33 increases MBNL1 and 2 transcript levels in DM1 myotubes and possible decrease DMPK levels.
Figure 11:
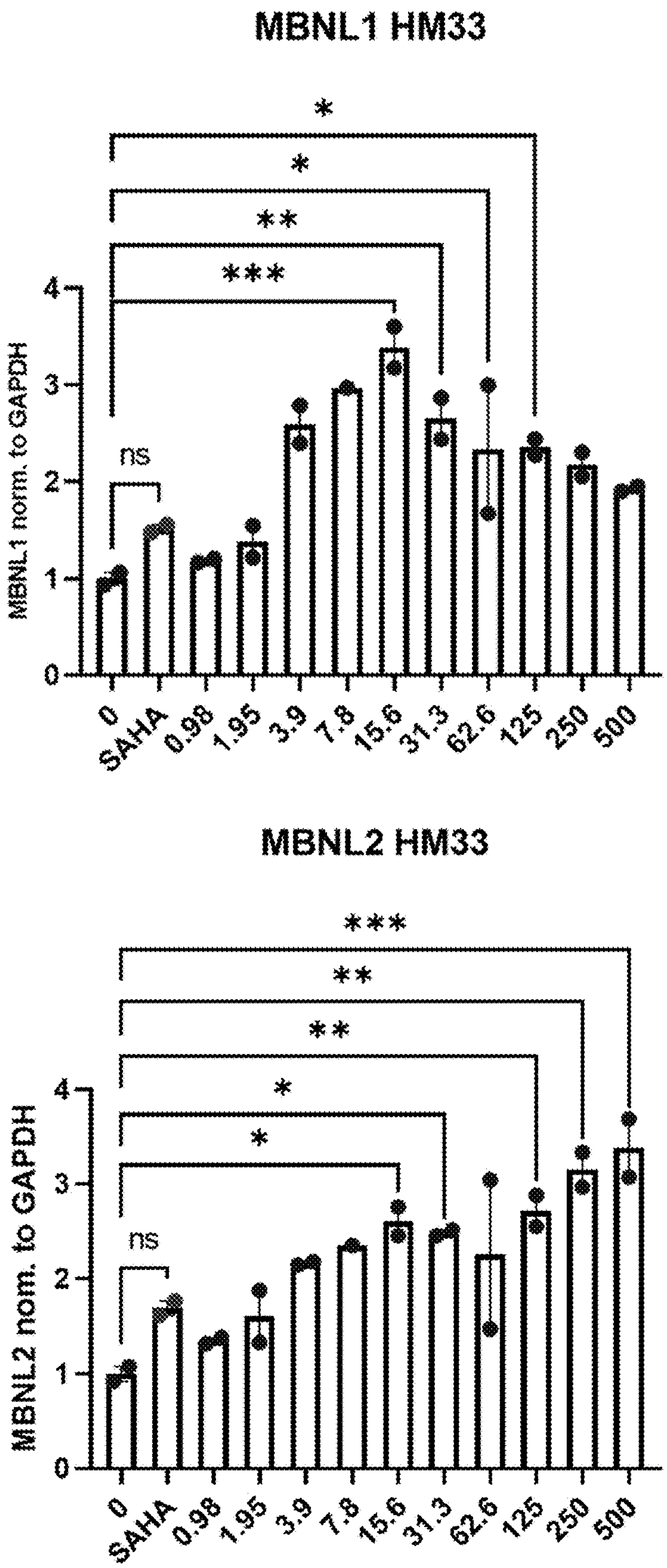
FIG. 11 presents HM33 increases MBNL1 and 2 transcript levels in control no. 2 myotubes.

Another aspect of the present disclosure is that embodiments open combinatorial approaches focused on all aspects of toxic RNA including transcription, up-regulation of MBNL, liberation of MBNL or cleavage of toxic RNA. Multiple pathways play important roles co-transcriptionally including: 1) actinomycin D mediated selective reduction of CTG expansion transcripts; 2) microtubule inhibitors mediated selective modulation of toxic CUG RNA levels; and 3) diamidine small molecule mediated reduction of toxic RNAs. In fact, data that a combination of small molecules targeting both transcription and blocking MBNL sequestration can be effective in splicing rescue in DM1 patient-derived cells and a DM1 mouse model, has been demonstrated by the inventors (PMID: 31485578). Like the diamidine compounds, MPCs likely work through at least two mechanisms, which is reducing the levels of the expanded CUG repeats and up-regulated MBNL proteins. In this regard, FIGS. 9-11 present supporting data, specifically, FIG. 9 presents graph analysis of SYNE1 and MBNL1 data directed to HM33 rescues mis-splicing in DM1 myotubes with 72-hour treatment. FIG. 10 presents graph analysis of HM33 increases MBNL1 and MBNL2 transcript levels in DM1 myotubes and possible decrease in DMPK levels, respectively. FIG. 11 presents graphic analysis that HM33 increases MBNL1 and MBNL2 transcript levels in control number 2 myotubes. In embodiments, combining embodiments, of the present disclosure with other therapeutic approaches facilitates lower dosing requirements overall thereby reducing costs, off-target effects and toxicity. The latter is especially relevant for diamidines, which have a known history of toxicity in humans. By developing new small molecules that build upon and complement an IMPEDE approach, embodiments include an innovative outcome-focused solution that is not limited by a particular predicted mechanism of action.

Many of the growing family of over 40 neuromuscular and neurodegenerative repeat expansion diseases, including myotonic dystrophy (DM), involve a strong RNA gain-of-function (GOF) mechanism with toxicity induced by expansion RNAs. In this mechanism, the expanded RNAs sequester RNA binding proteins (RBPs) leading to the disruption of multiple downstream RNA processing pathways. The reduction of the expanded RNAs to alleviate disease mechanism and downstream pathogenesis is therefore an attractive therapeutic approach. Small molecule efficacy has been shown including: (1) actinomycin D mediated selective reduction of transcription from expanded CTG repeats; (2) microtubule inhibitors mediated selective modulation of toxic CUG RNA levels; and (3) diamidines mediated reduction of toxic RNAs. While these results show promise, many of these compounds are toxic and display sub-optimal properties leading to the development of a new set of modified polycyclic compounds (MPCs). The MPCs of the present disclosure are based on three elements: a heterocyclic core; a benzimidazole side group; and functionalized end groups. Modifying each of these elements provides a large panel of compounds to aid in understanding a mechanism of action and develop new drug candidates to address the urgent unmet therapeutic need in DM. Preliminary data for two MPCs shows robust rescue of splicing in both DM1 and DM2 cell lines in the nanomolar range with little associated toxicity or effects on cell viability as well as rescue of mis-splicing in 2 independent DM mouse models. Parallel in vitro and in vivo design-model-test cycles are used to systematically modify and evaluate a series of compounds to better understand their mechanism of action and test their therapeutic potential in DM patient-derived cell lines and animal models.

Designing, Modelling, and Synthesizing a Panel of New Modified Polycyclic Compounds (MPCs) with Improved Activity, Solubility and Target Engagement.

Two MPCs (HM19A & HM19B depicted in FIG. 2A) of the present disclosure demonstrate improved splicing rescue in multiple DM models. To refine these new compounds and generate a panel of candidate molecules for further testing (See e.g., FIG. 1, step 1) molecular modeling is used to understand how MPC embodiments interact with DNA and RNA DM repeats (CTG/CUG & CCTG/CCUG); synthesize further derivatives with modifications to each element (core, side & end groups) with a focus on functionalized end groups for HM19A & 19B to understand and enhance repeat interactions, water solubility and bioavailability; (See e.g., FIG. 1, step 1) in vitro characterize compounds for their binding affinity to DNA/RNA substrates (isothermal calorimetry), their solubility and effect on the thermal stability of DNA/RNA substrates (UV melting), ability to disrupt RBP-CUG repeat complex in vitro; and assess selective reduction of expanded CUG repeats and splicing rescue in a HeLa DM1 cell model. Impact: Identifying small molecule elements that increase binding to DM repeats and selectively reduce CUG repeat levels aids in understanding mechanism of action and providing strong lead compounds for advanced in cellulo-efficacy studies.

Characterizing the Best-In-Class MPCs for in Cellulo Activity and Therapeutic Potential.

To understand the mechanism of action and prioritize lead MPCs, in cellulo activity is evaluated. (See e.g., FIG. 1, and FIG. 1 at step 2). Starting with MPCs (HM19A & 19B (See FIG. 2A) and expanding to other MPCs identified, DM1 and DM2 patient-derived cell lines are used to show, inter alia, splicing rescue of DM1-specific, DM2-specific and shared cassette exon mis-splicing events; expression levels of DM expanded and wildtype alleles, MBNL and RBFOX transcripts and proteins; distinguish effects on transcription from RNA turn-over; on- and off-target transcriptomic effects (RNAseq); and toxicity and effects on cell viability. Given that DM is a multi-system disorder with strong CNS involvement, assessing brain uptake potential using the well-known MDR1-MDCK monolayer assay is employed. Together these data refine the model-design-test cycle and identify candidate MPCs for studies in DM animal models. Impact: Characterizing lead candidates for their potential impact on DM advances the understanding of disease biology, reveals new therapeutic avenues and identifies suitable candidates for pre-clinical studies.

Determining the Bioavailability, Splicing Rescue, and Therapeutic Potential of Lead Candidate MPCs in Two DM1 Mouse Models.

Two DM1 mouse models (HSALR for muscle and Dmpk480/480 for CNS) are used to test in vivo splicing rescue and therapeutic potential of the best-in-class MPCs. Data from lead candidate MPCs (N=6-12) after 1-week short-term treatment is compared to baseline diamidine data for: (1) splicing rescue of specific (RT-PCR) and global events (RNAseq); (2) RNA foci, transcript levels and MBNL sequestration; and (3) bioavailability (MS analysis) and toxicity (weight and histopathology). Select candidates (N=2-5) with largest splicing rescue and least off-target effects will be used for 3-month long-term studies, to evaluate the above measures plus DM muscle pathology (HSALR only) via EMG myotonia and grip strength. In embodiments, the methods of the present disclosure identify the candidate(s) with the best therapeutic potential defined as: high splicing rescue; abundant multi-organ bioavailability; cross-platform molecular and histopathological rescue; low toxicity; and limited off-target effects. Impact: Determining the long-term therapeutic potential of lead compounds is an important step in understanding the in vivo mechanism of action and a critical step towards future clinical studies.

Research Strategy and Feasibility

In embodiments, methods of the present disclosure use parallel in vitro and in vivo design-model-test cycles (See FIG. 1) to systematically modify and evaluate a new class of compounds to better understand their mechanism of action and test their therapeutic potential in DM patient-derived cell lines and animal models (See e.g., FIG. 1, steps 2 and 3). In embodiments, the inventors generate a new class of compounds to improve efficacy and reduce toxicity, the latter of particular importance given the known toxicity of the well-studied diamidine class of molecules. To leverage previous findings and move beyond diamidines, the inventors focus on building this new class of compounds (MPCs) around three core elements: a heterocyclic core; a benzimidazole side group; and functionalized end groups. Initial lead compounds, (HM19A & HM19B) were built around a heterocyclic furane core with a benzimidazole side group and end groups (unmodified for HM19A or methylpiperazine for HM19B) to test the effects of molecule length. Additional MPCs modify each element using a systematic and logical cycle of design, modeling and testing. After running initial lead MPCs, HM19A and HM19B, through a testing pipeline (See FIG. 1), significant improvements are observed in splicing rescue with little toxicity across multiple model systems.

Figure 2A:
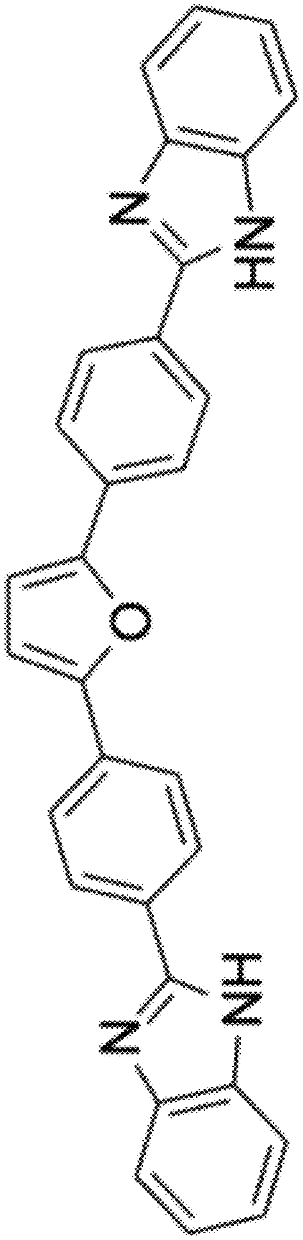
FIGS. 2A-2E depict splicing rescue of polycyclic compounds of the present disclosure, such as polycyclic compounds of the present disclosure referred to as HM19A and HM19B, across multiple DM model systems.
Figure 2A:
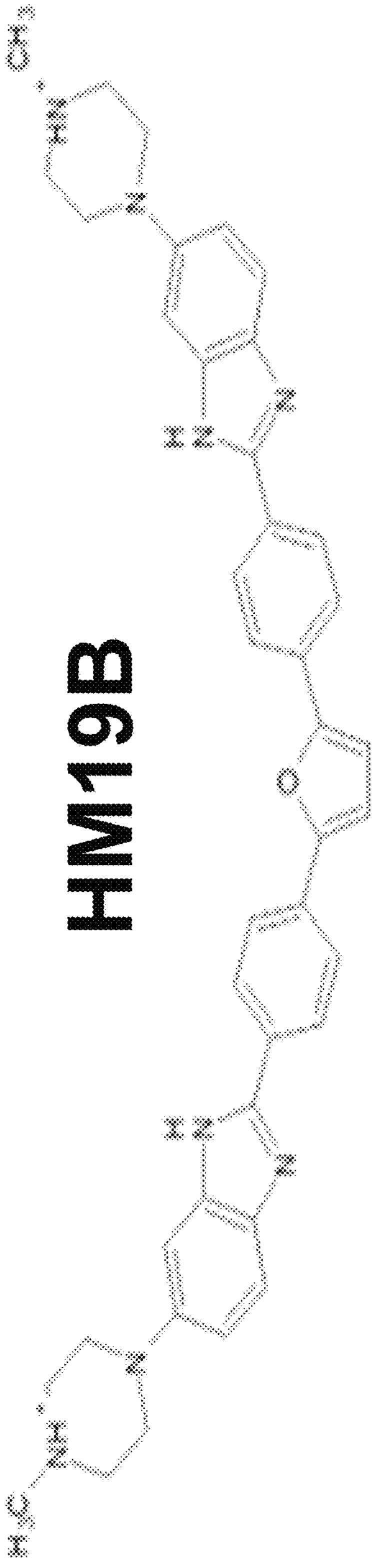
Figure 2B:
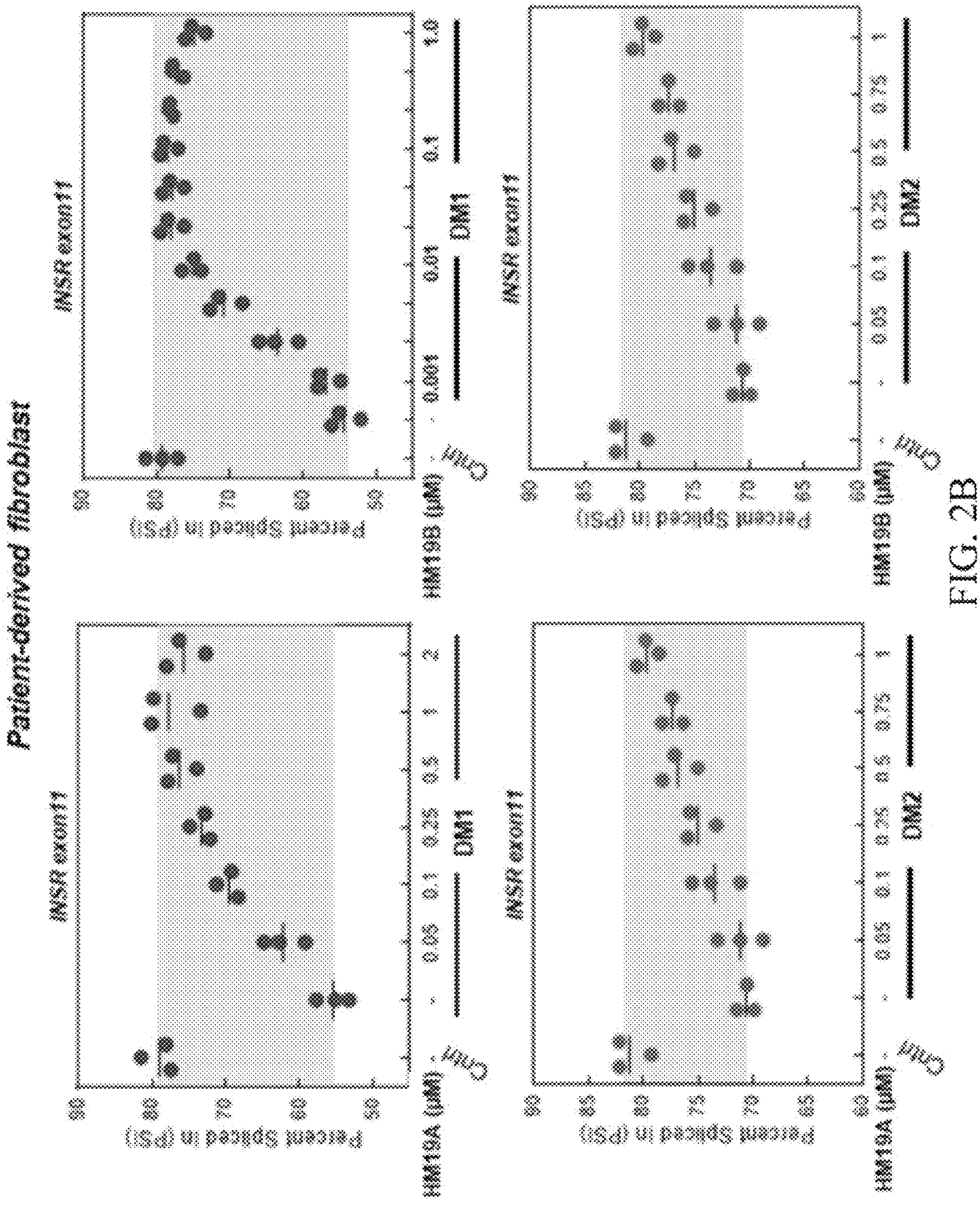
Figure 2C:
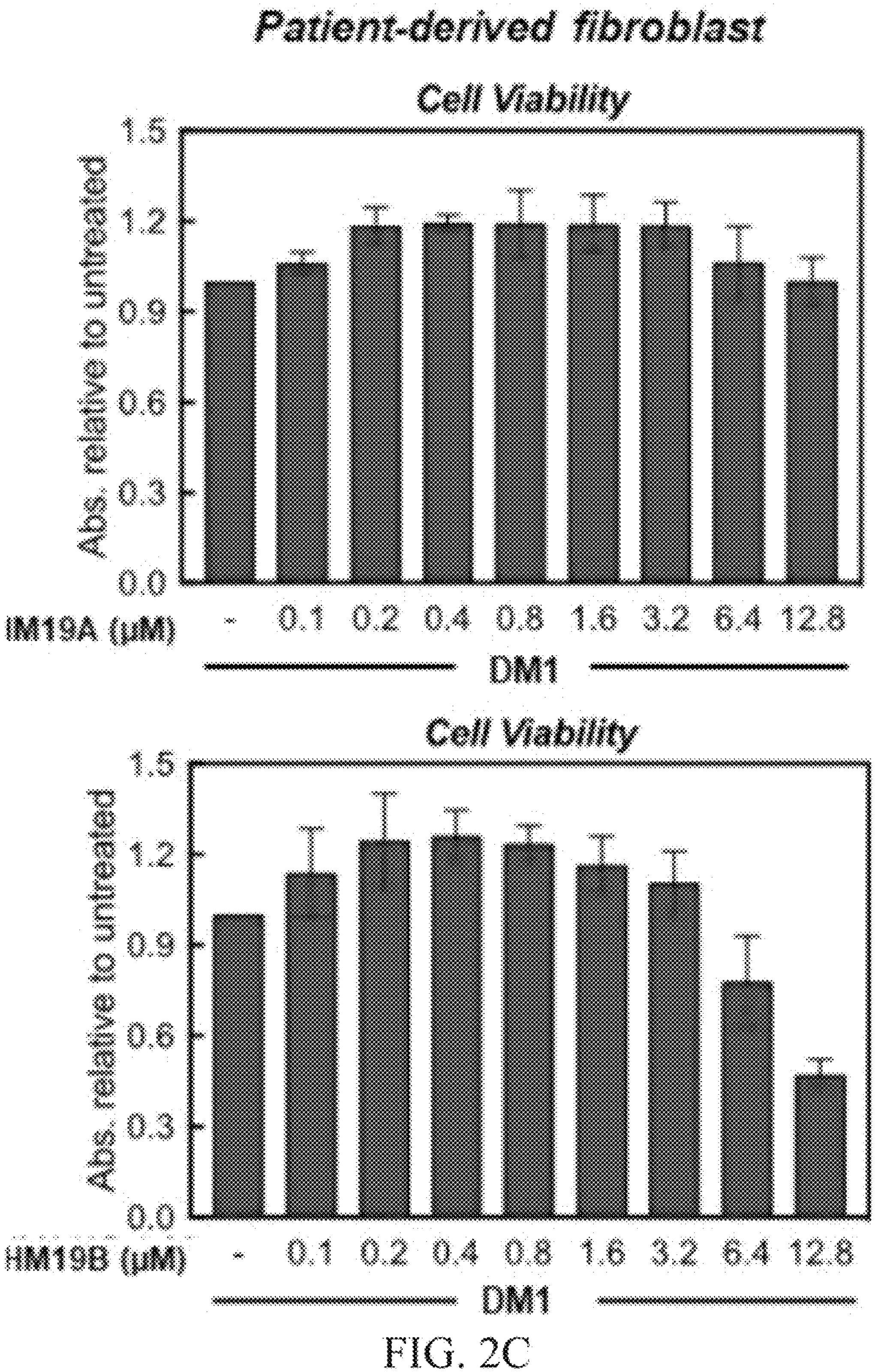

FIG. 2A-2E present splicing rescue of MPCs HM19A and HM19B across multiple DM model systems. FIG. 2A presents the chemical structures of furamidine, HM19A and HM19B. FIG. 2B presents RT-PCR analysis of INSR exon 11 mis-splicing in DM1 and DM2 fibroblasts treated with HM19A (left) or HM19B (right) shows strong rescue. FIG.

Figure 2D:
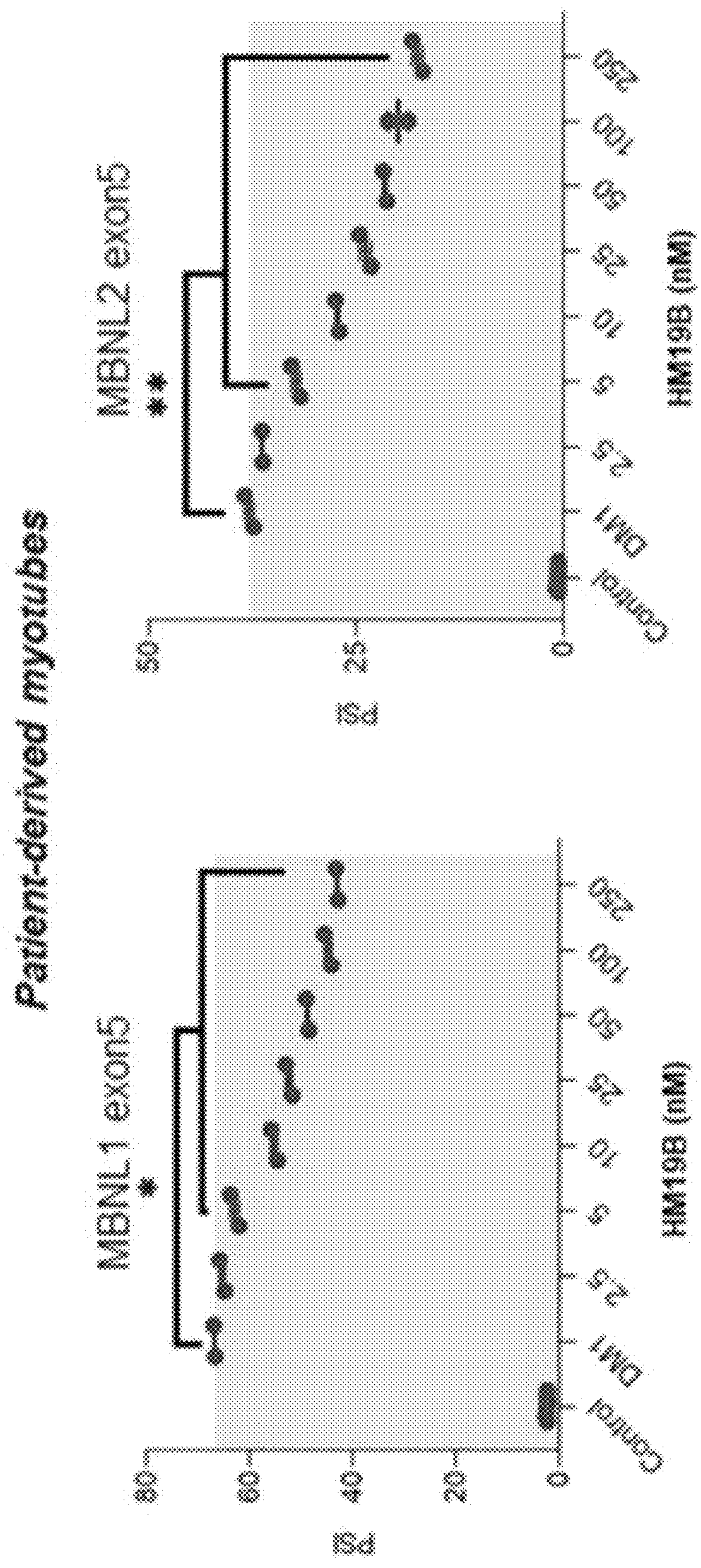
Figure 2E:
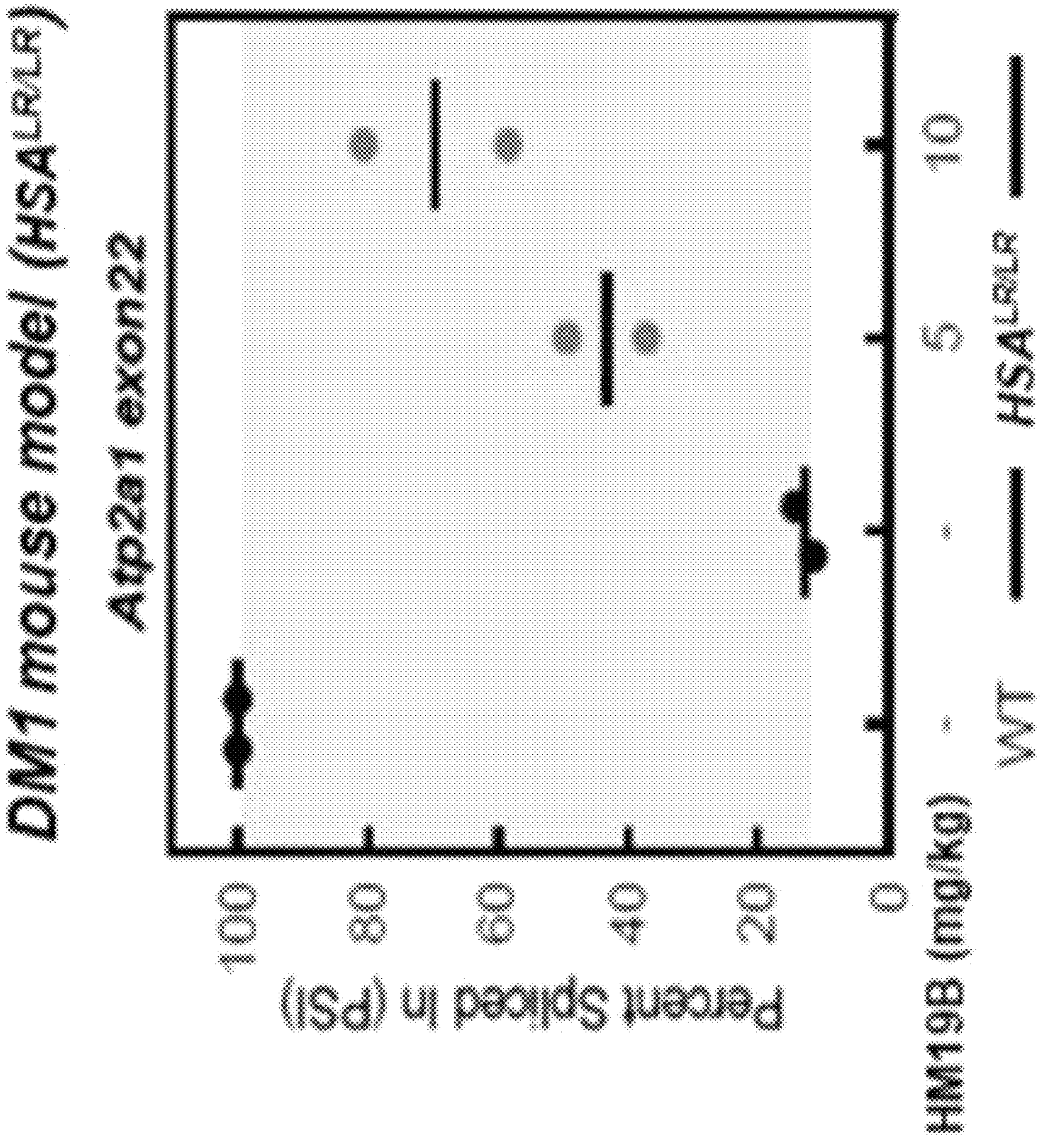

2C presents MTT cell viability for HM19A (top) and HM19B (bottom) in DM1 fibroblast shows no effect on viability at low micromolar concentrations. FIG. 2D presents RT-PCR analysis of MBNL1 exon 5 (left) and MBNL2 exon 5 (right) mis-splicing events in DM1 myoblasts shows promising rescue by HM19B at nanomolar concentrations. FIG. 2E presents RT-PCR analysis of Atp2a1 exon 2 mis-splicing in RNA harvested from tibialis anterior from the $HSA^{LR/LR}$ shows robust splicing rescue. (ANOVA two-tailed test, $*p<0.05$ and $**p<0.01$).

In embodiments, the methods of the present disclosure are suitable to design, model and synthesize a panel of new modified polycyclic compounds (MPCs) with improved activity, solubility and target engagement.

Modeling MPCs binding to repeats: To guide the synthesis of new compounds, molecular modeling of HM19A/19B and other MPCs bound to CTG/CUG and CCTG/CCUG repeats is performed. Synthesizing derivatives of these compounds is guided by in silico modeling of the interactions of HM19A/19B and analogs with DNA and RNA repeats.

Figure 3:
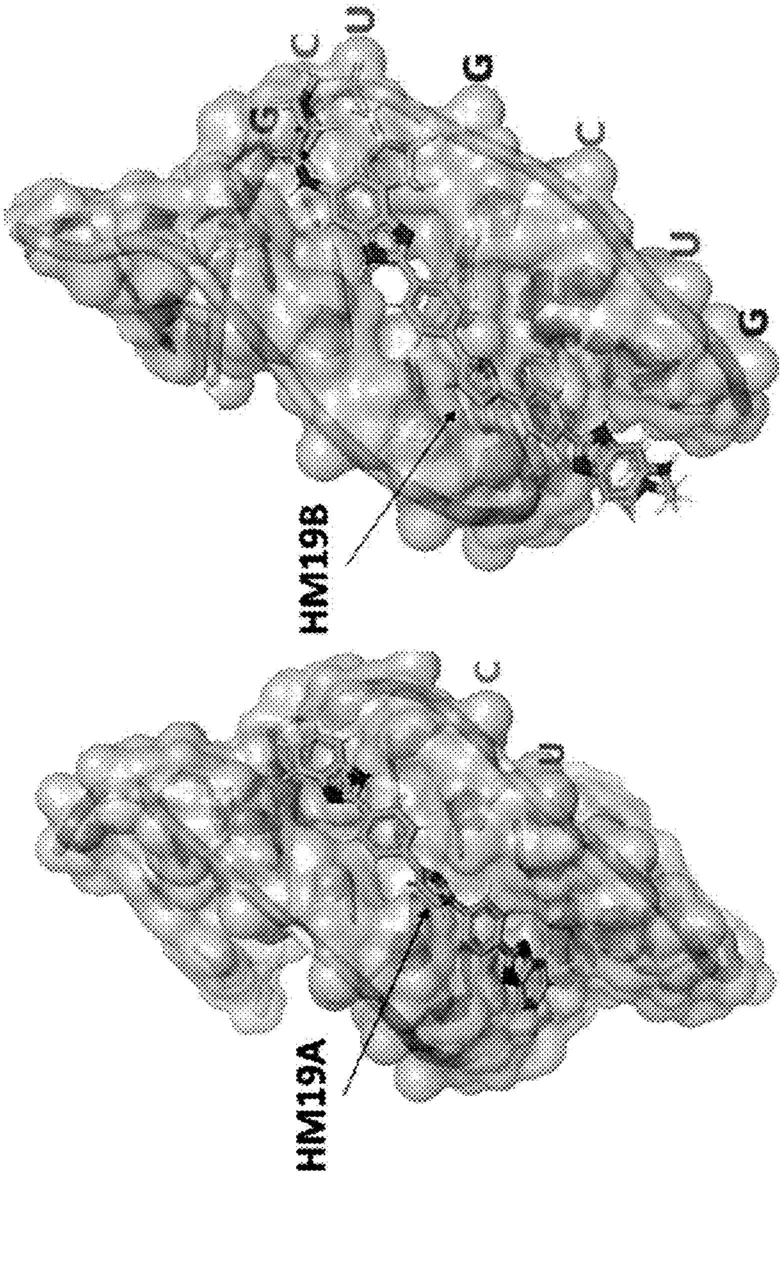
FIG. 3 depict docked complexes of polycyclic compounds of the present disclosure, such as polycyclic compounds referred to as HM19A and HM19B, with CUG repeat duplex RNA.

An initial unrestrained docking of a single HM19A or HM19B molecule to the CUG repeat RNA duplex structure (PDB ID:5MWI) results in both compounds binding to the minor groove with high docking scores. As such, FIG. 3 presents 3D-docked complexes of HM19A and HM19B with CUG repeat duplex RNA. Modeling of HM19A (left) and HM19(B) with CUG duplex shows both compounds bind the minor groove with high docking scores. HM19A spans exactly 2 U-U mismatches whereas HM19B spans 2 and 3 U-U mismatches. Positive charged piperazine group in 19B provide backbone interactions. Further, it is noted that analysis of circular dichroism (CD) spectroscopy of the HM19B compound with the CUG repeat RNA confirms that there is a surface interaction between ligand and substrate. These preliminary structures provide a framework for the synthesis of analogs to optimize interactions with the CUG repeats.

CUG repeats are known to adopt stable hairpins with GC base-pairs interrupted by U-U mismatches, so a rigid body approach is used for the docking studies. However, to assess the flexibility of the binding interface, especially in case of RNA, an ensemble of structures of the repeats is generated via molecular dynamic (MD) simulations, using GROMACS39. Clustering analysis is used to obtain the top three dominant structures from the ensemble and each structure is used to obtain a docked complex of HM19A and HM19B with the CUG repeats and CTG repeats and analyses is extended to CCUG/CCTG repeats. By combining the results of MD simulations and docking, a representative structural model(s) of the repeat:HM19A and repeat:HM19B complexes is constructed. Representative structures to test the different derivatives of HM19A and HM19B, is performed by docking them at the interaction site of HM19A/HM19B with the repeats. The efficiency of binding of the different analogs synthesized is assessed by comparing the docking scores for each of the derivatives to the repeats. For the selected top hits, based on the docking scores, free energy perturbation (FEP) simulations is used to calculate the difference in the binding free energy for each of the derivatives. FEP simulations provide a more accurate estimate of the binding free energies compared to docking scores, especially when studying the effects of adding or deleting small functional groups and have been successfully used for similar studies.

Figure 4A:
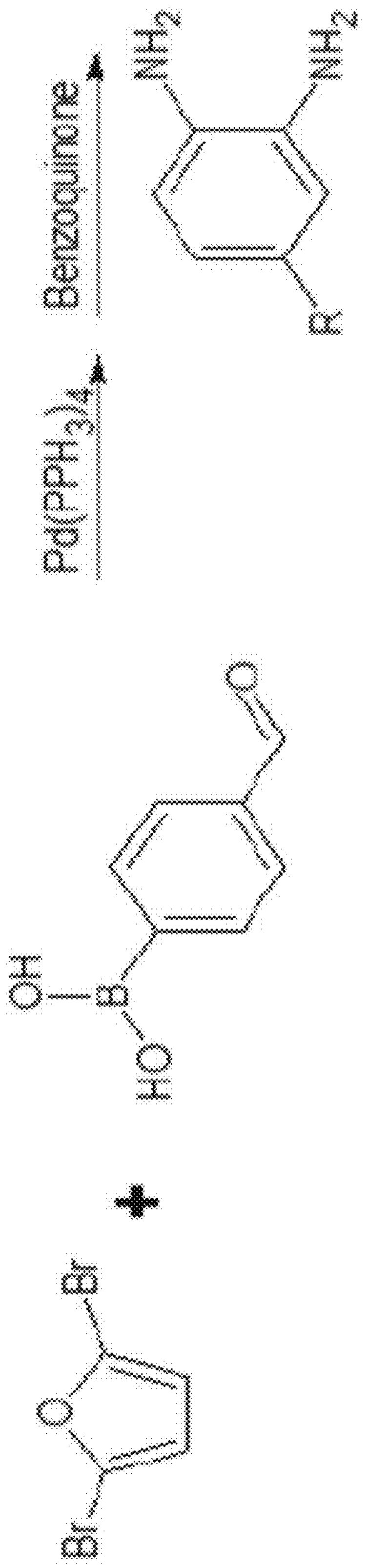
FIGS. 4A-4C depict a synthesis scheme for polycyclic compounds referred to as HM19A and HM19B and associated modified polycyclic compounds of the present disclosure.
Figure 4B:
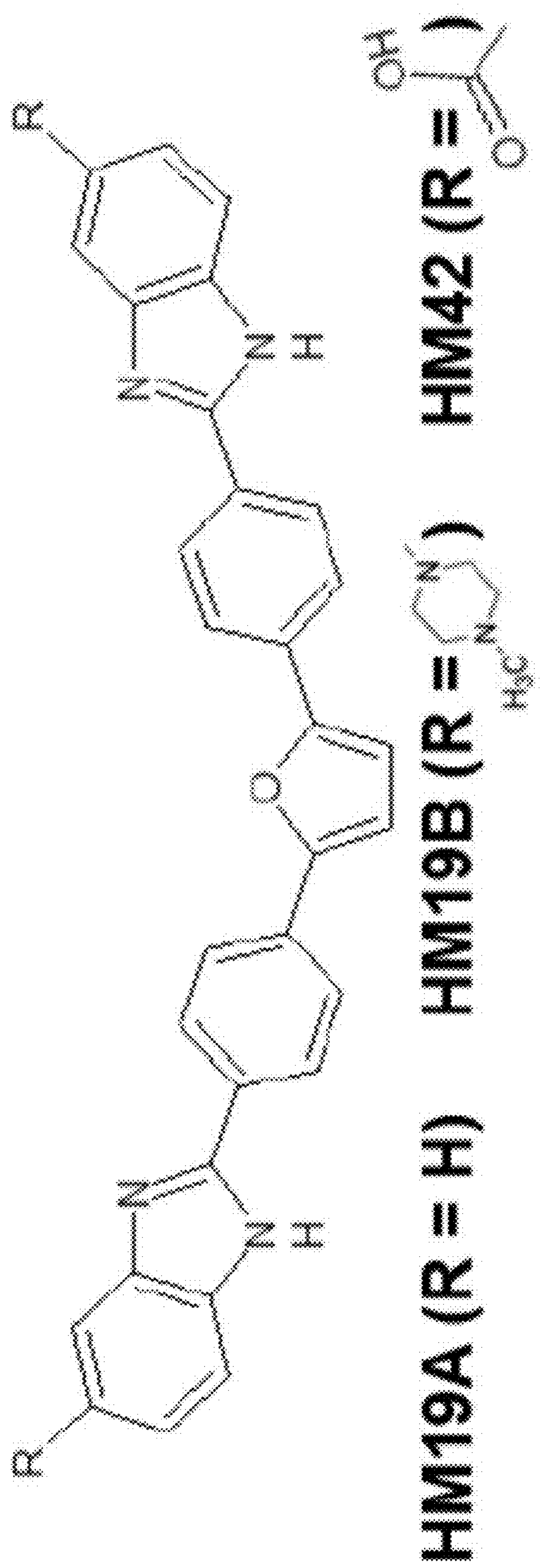
Figure 4C:
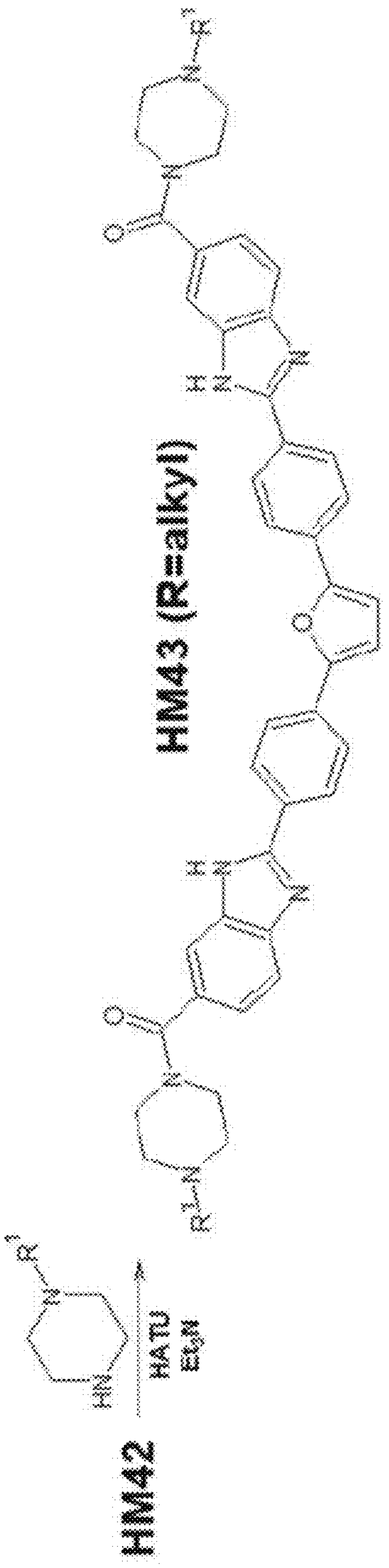

Synthesis of new MPCs and HM19A/HM19B analogs: The inventors synthesized HM19A and HM19B (See e.g., FIG. 4) and multiple other MPCs (See e.g., FIG. 5). Synthesis of MPCs is focused on rationally adding or removing select functional groups from the parent compounds to enhance specific repeat interactions. Existing synthetic protocols and modeling around Hoechst 3325842 is used to provide insights and direct a path towards the synthesis of lead molecules, HM19A & HM19B. Moving forward, existing literature and predictive tools, such as Marvin cheminformatics software (ChemAxon), is used to aid in the design of new MPCs that will be used to test for improvements in water solubility, bioavailability and increased blood brain barrier (BBB) penetration. An initial focus will be on modifications to HM19A/HM19B, using in silico modeling and the results from the in vitro and in vivo studies to guide modification selection. For example, in embodiments, the benzenes are changed to pyridine rings in HM19B to generate HM33 and other derivatives (See e.g., FIG. 5) as a similar modification to furamidine significantly improved BBB penetration. Additional modifications to MPCs including HM19A/HM19B is made to the furan core, benzimidazoles and end groups with a focus on understanding how these molecules interact with CUG/CCUG and CTG/CCTG repeats. Modifications that enhance binding and splicing rescue are prioritized as well as those that maintain water solubility and bioavailability, utilizing data from e.g., the process sequence of FIG. 1, Steps 2 and 3 to provide feedback into the modification design and synthesis. All synthesized MPCs are characterized using mass spectrometry and NMR to confirm identify and purity of molecules before testing.

Modeling of HM19A/HM19B analogs is used to identify potential new H-bond donor and acceptors that interact with CUG/CCUG and CTG/CCTG repeats. 40-50 derivatives are anticipated (See e.g., FIGS. 5A and 5B) with the same modifications made to HM19A and HM19B to help determine how the modification impacts function of the small molecules. For some of these compounds, the inventors take advantage of their fluorescent nature to be able to qualitatively rapidly determine their cellular localization. Mass spectrometry will be used to quantitatively monitor compound distribution in cells/media and across tissues.

The Novel MPCs are Characterized to Determine Activity and Specificity in the Sub-Aims Below.

MPCs and nucleic acid binding: To determine the binding affinity between RNA and DNA substrates and MPCs, isothermal titration calorimetry (ITC) is used. The approach is well suited for studying the binding of small molecules to larger macromolecules and has been previously utilized by us and others to study the interaction of diamidines with DNA or RNA duplexes. The binding of each analog is determined for both DNA (CTG/CAG, CCTG/CAGG) and RNA (CUG/CAG, CCUG/CAGG) duplexes via ITC under conditions that favor structure formation. Small molecule binding is performed with the control sequences, including AT rich sequences that are the preferred binding site for furamidine and other diamidines.

To determine if MPC binding changes the thermal stability of DNA/RNA substrates, UV melting curve analysis is utilized, which is common for small molecule interactions with nucleic acid. This technique tells if HM19A/HM19B and other MPCs stabilize DNA and RNA duplexes and the degree of stabilization. Results of the thermal stability is correlated with in vivo CUG levels (See e.g., FIG. 1) and splicing (See e.g., FIG. 1 step 2) to determine if there is a correlation between increased thermal stability and degree of splicing rescue.

To determine if MPCs disrupt CUG/CCUG-MBNL1 complexes, a gel shift assay with purified MBNL1 and CUG/CCUG repeats is utilized. A concentration gradient of MPCs, from which inhibition constants (Ki) is determined to compare activity of different MPCs. The gel shift assay is performed as done previously with furamidine. In embodiments, the MPCs bind to CUG/CCUG repeats with significant preference over proteins. ITC is used to determine if MPCs directly bind MBNL1. To determine if MPCs selectively disrupt MBNL1—CUG/CCUG complexes compared to MBNL1—pre-mRNA interactions, single-stranded RNA substrates (run of uridines with 1 or 2 GC motifs) that mimic pre-mRNA binding sites is used to determine if MPCs can disrupt this MBNL-RNA complex. A gel shift assay with MBNL1 and RNAs that mimic pre-mRNA binding sites is used.

Figure 6A:
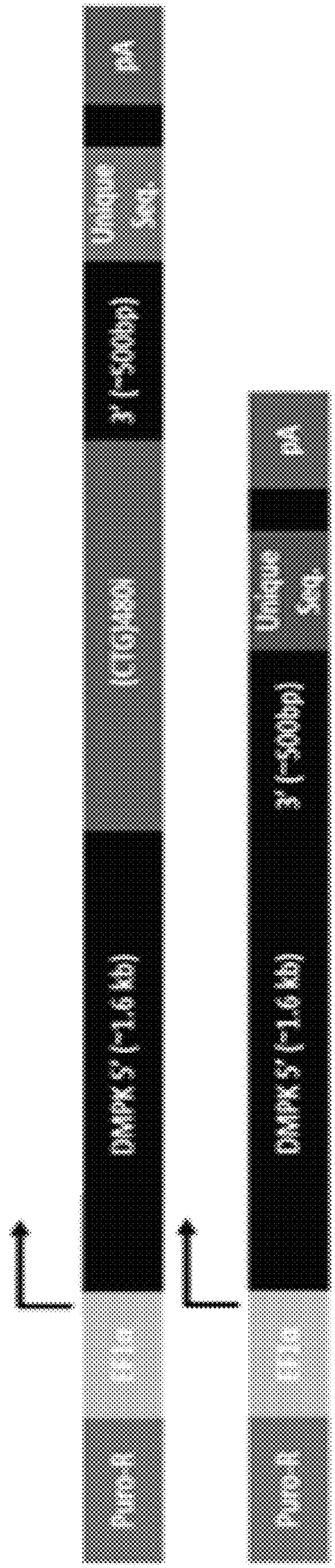
FIGS. 6A-6C depict a HeLa DM1 screening cell line.
Figure 6B:
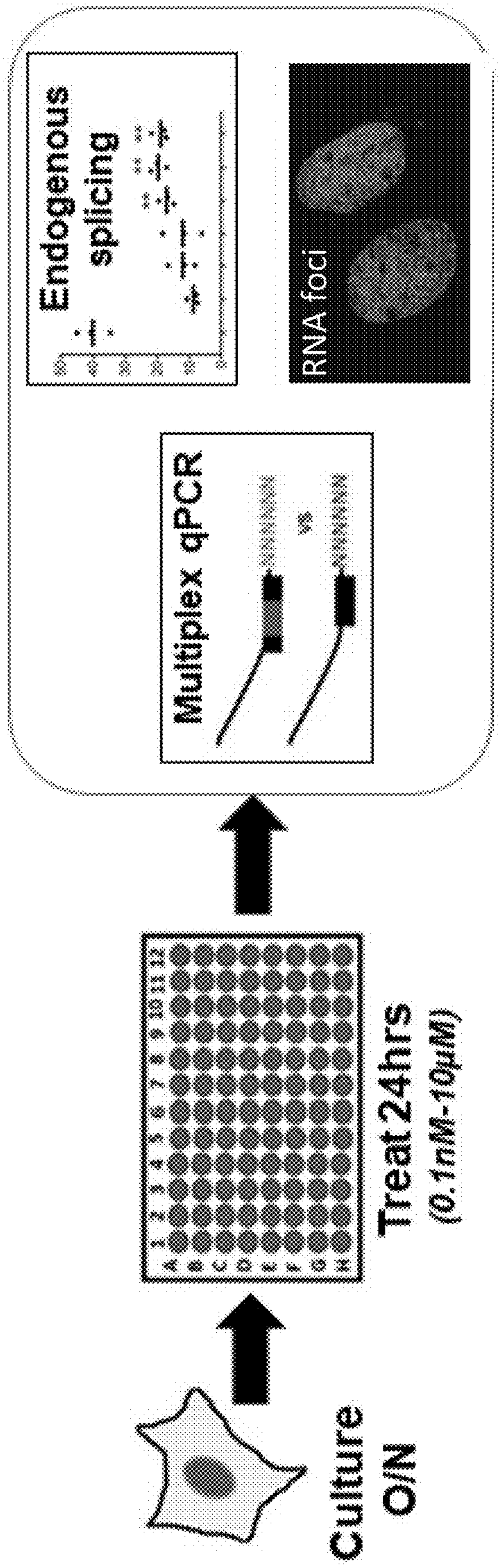
Figure 6C:
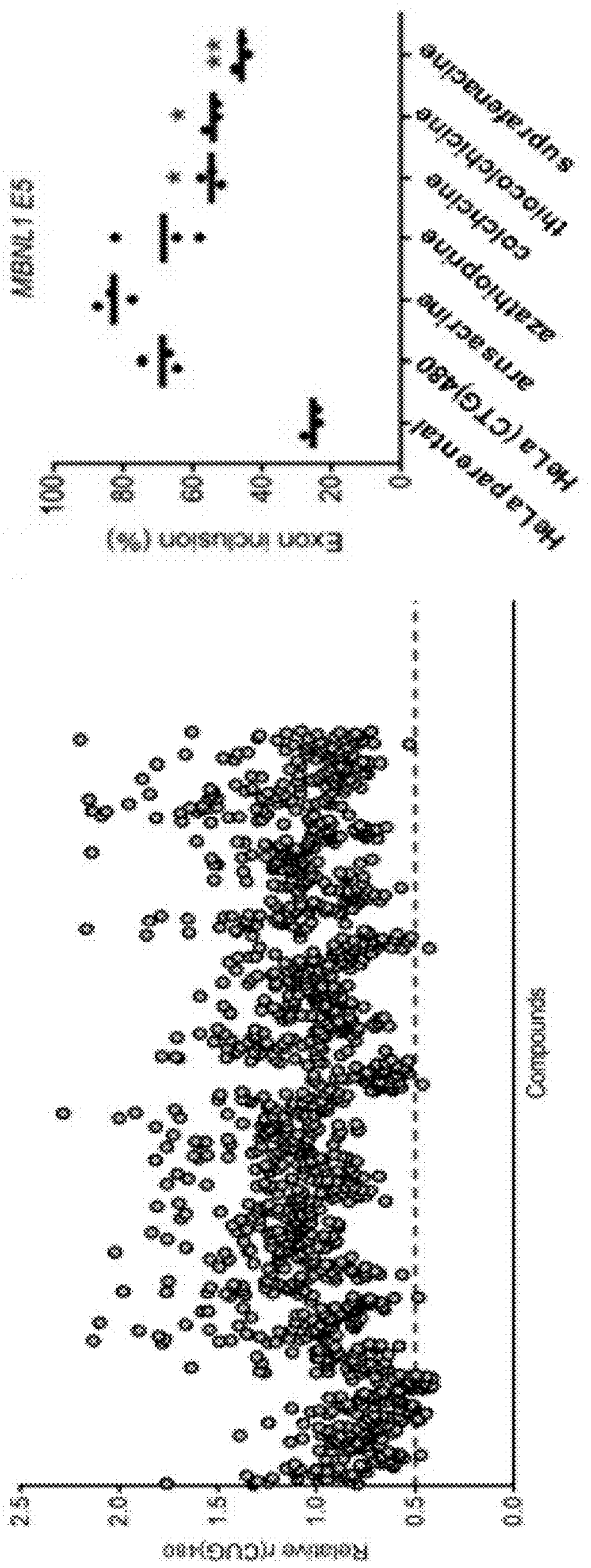

MPCs treatment selectively reduce expanded CUG levels. To determine if MPCs reduce toxic RNA levels and possibly work through IMPEDE, a recently established CTG repeat expansion-selective screening platform is used. Engineered DM1 HeLa cells are used to contain both an interrupted (CTG)480 repeat tract consisting of 24 modules of [(CTG) 20(CTCGA)] and a (CTG)0 control tract driving expression from the human EF1α promoter. In this regard, FIG. 6A presents HeLa DM1 screening cell line with constructs used to generate the DM1 HeLa cell model for repeat-selective screening. Constructs are identical except for the (CTG) 480i, an interrupted repeat tract consisting of 24 modules of [(CTG)20(CTCGA)] and a unique sequence (21-bp qPCR probe target and 8-bp barcode). FIG. 6B presents screening pipeline for MPCs in the HeLa $CTG_{480}$ DM1 cell line with output analysis of multiplex qPCT, endogenous splicing and/or RNA foci, and FIG. 6C presents hits from HeLa $CTG_{480}$ screen of LOPAC library and RT-PCR splicing analysis of top microtubule inhibitor hits for MBNL1 exon 5.

Both constructs contain exons 11-15 of human DMPK48, each with a unique qPCR probe binding site 3' of the repeat tract to distinguish the two transcripts produced (FIG. 6A). These constructs permit the sensitive ratio-metric measurement of r(CUG)480 abundance relative to r(CUG)0. Multiplex RT-qPCR is performed where the same primer is used to reverse transcribe both RNA species and the same primer pair is used in the qPCR reaction but with different fluorescent probes against the unique sequences to sensitively distinguish r(CUG)480 from r(CUG)0 abundance in the same reaction. These cells comparably express both (CUG) 480 and (CUG)0 RNA permitting CUG repeat-selective screening and display cellular hallmarks of DM1 including ribonuclear foci (FIG. 6B). Screening the commercial LOPAC small molecule library (Sigma-Aldrich LO1280) using this assay identified colchicine and broadly microtubule inhibitors (FIG. 6C) as a class of novel small molecules that rescue DM1 splicing in patient-derived myotubes and the HSALR/LR mouse model. Colchicine will be a positive control for the proposed studies with HM19A/HM19B and derivatives (MPCs). Broad concentration ranges will be used to initially determine if MPCs selectively reduce toxic CUG levels in the HeLa DM1 cell model.

Rigor and Reproducibility: MPCs are tested using identical assays across multiple batches with statistical analyses to ensure results are robust and reproducible. ITC, thermal melts and gel shift assays are done at least in triplicate at each condition/concentration and appropriate statistical analyses to assess significance. All HeLa DM1 cell model testing of MPCs include a minimum of 3 biological and 3 technical replicates across multiple independent MPC preparations to minimize batch effects. Means of individual treatment groups are calculated with standard deviation and then compared to means of control treatment groups (vehicle treated) using appropriate statistical measures.

Expected outcomes and alternative approaches: Based on the preliminary data with HM19A/HM19B a range of activity and biophysical properties from MPCs is found that will guide future modifications. Challenges with the synthesis of HM19A and HM19B analogs are not expected because similar types of modifications have been made to other small molecules, such as diamidines.

The ITC and thermal melt studies determine the binding affinity and specificity of MPCs for CUG/CCUG and CTG/CCTG repeats. An alternative and complementary approach to the computer modeling is to solve crystal or NMR structures of MPCs in complex with the CUG/CCUG and CTG/CCTG repeats. Testing the MPCs in the HeLa DM1 cell line will determine if these molecules potentially work through IMPEDE or other mechanisms (such as releasing sequestered MBNL). Gel shift competition assay combined with biophysical characterization of MPCs with repeats is expected to provide insights into the mechanism of action of the MPCs. If high affinity binding of an MPC to CUG/CCUG repeats is observed as well as disruption of the MBNL1-CUG/CCUG repeat complex at nanomolar concentrations, these results would be consistent with this MPC working at the level of binding the expanded repeats. If one finds similar binding affinities to RNA and DNA repeats and reduction of CUG repeats in the HeLa DM1 cell line, these results would be more consistent with the IMPEDE approach. HM19B's promising (See e.g., FIGS. 2A-2E) splicing rescue at the nanomolar concentration in DM fibroblasts and myotubes suggests the MPC is an excellent compound, but it remains of interest to define the mechanism of rescue and determine if more active analogs of HM19B exist.

Referring to FIG. 1, Step 2, a process flow includes characterizing the best-in-class MPCs for in cellulo activity and therapeutic potential. Rationale and preliminary data: Because of the multisystemic nature of pathogenesis in myotonic dystrophy, it is desirable to evaluate the therapeutic potential of excellent MPCs in multiple DM cellular models as well as in control models in order to best prioritize compounds for in vivo testing. The cellular activity of MPC lead panel is systematically evaluated starting with HM19A & HM19B in 2 independent DM1 and DM2 patient-derived fibroblast lines and 2 independent DM1 myoblast/myotube differentiation models along with age and gender-matched control cell lines. Potential blood brain barrier penetrance is evaluated using the established MDR1-MDCK monolayer assay. This aim will facilitate the informed selection of the top performing compounds in cellular studies for testing in animal models of DM (See e.g., FIG. 1, step 3).

Figure 7A:
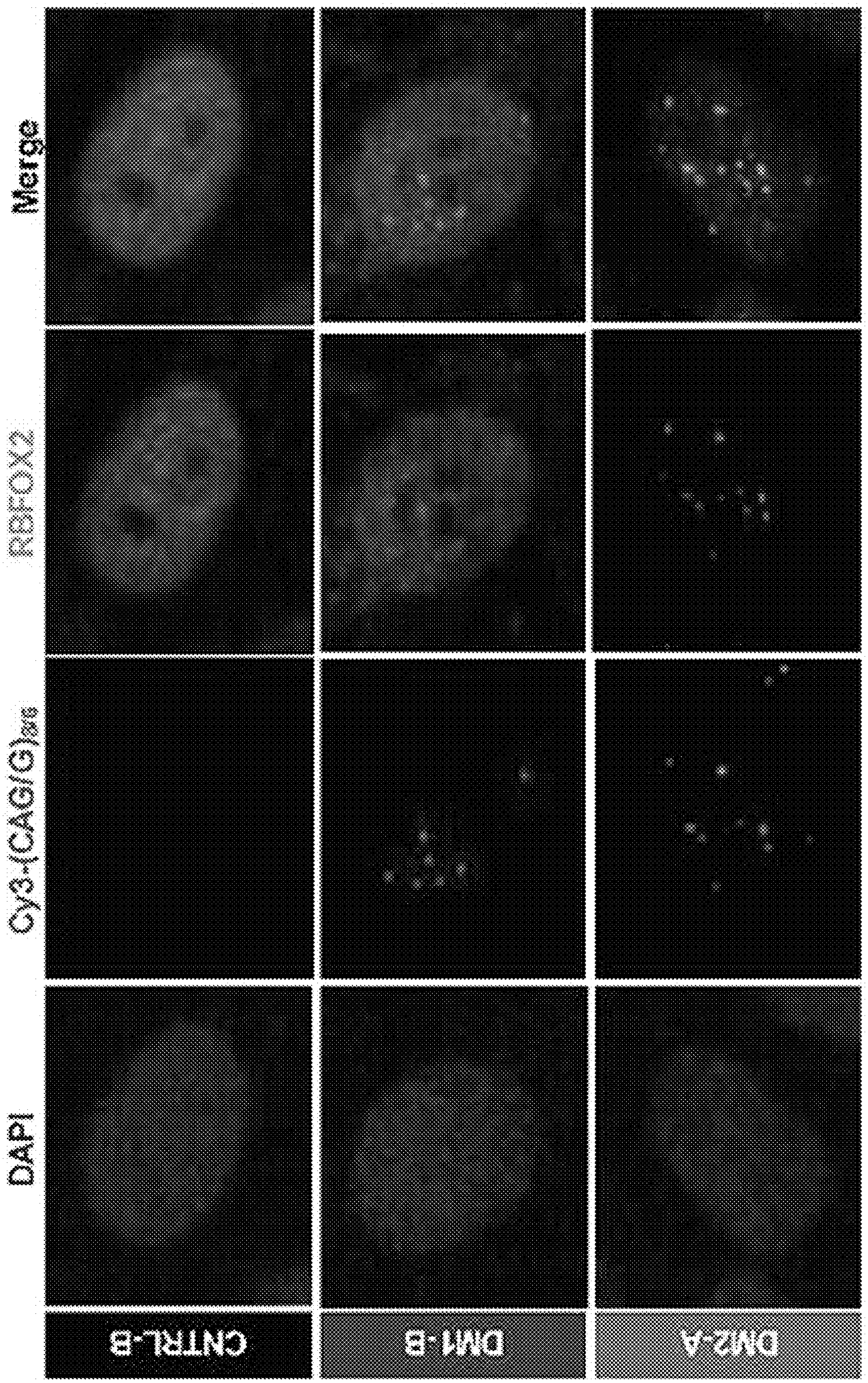
FIGS. 7A-7F depict patient-derived DM1 and DM2 fibroblasts displaying molecular markers of disease.
Figure 7B:
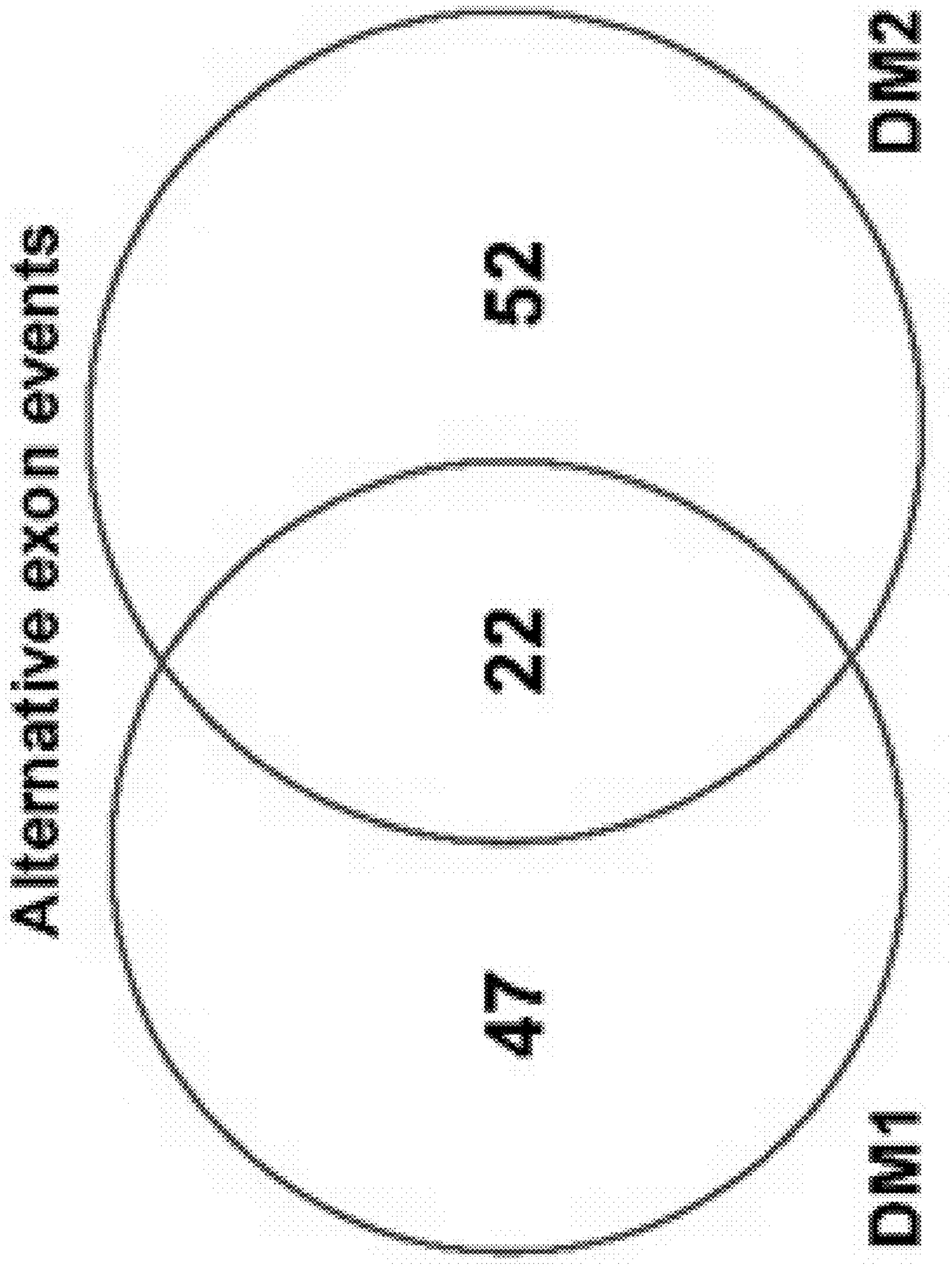
Figure 7C:
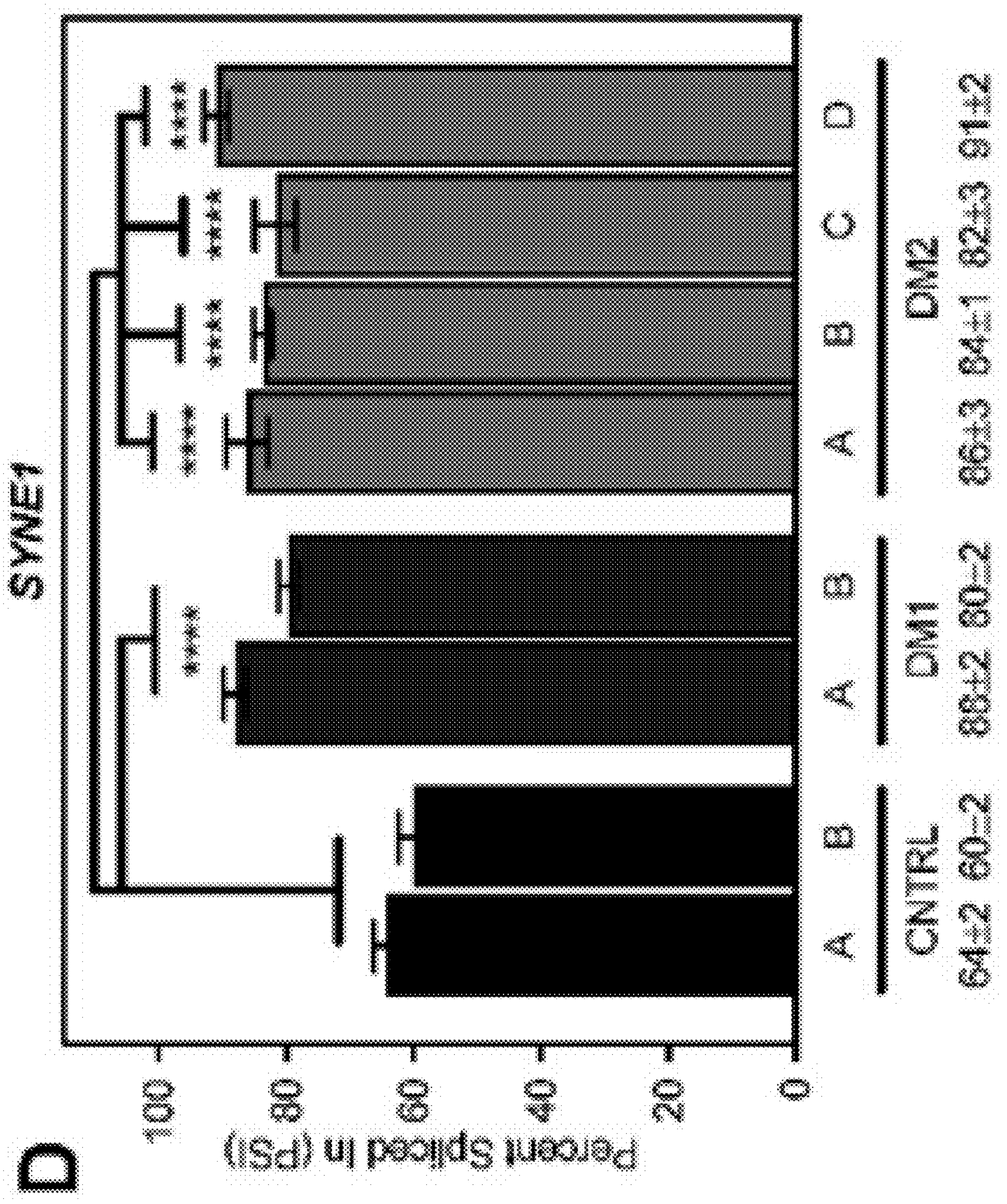
Figure 7D:
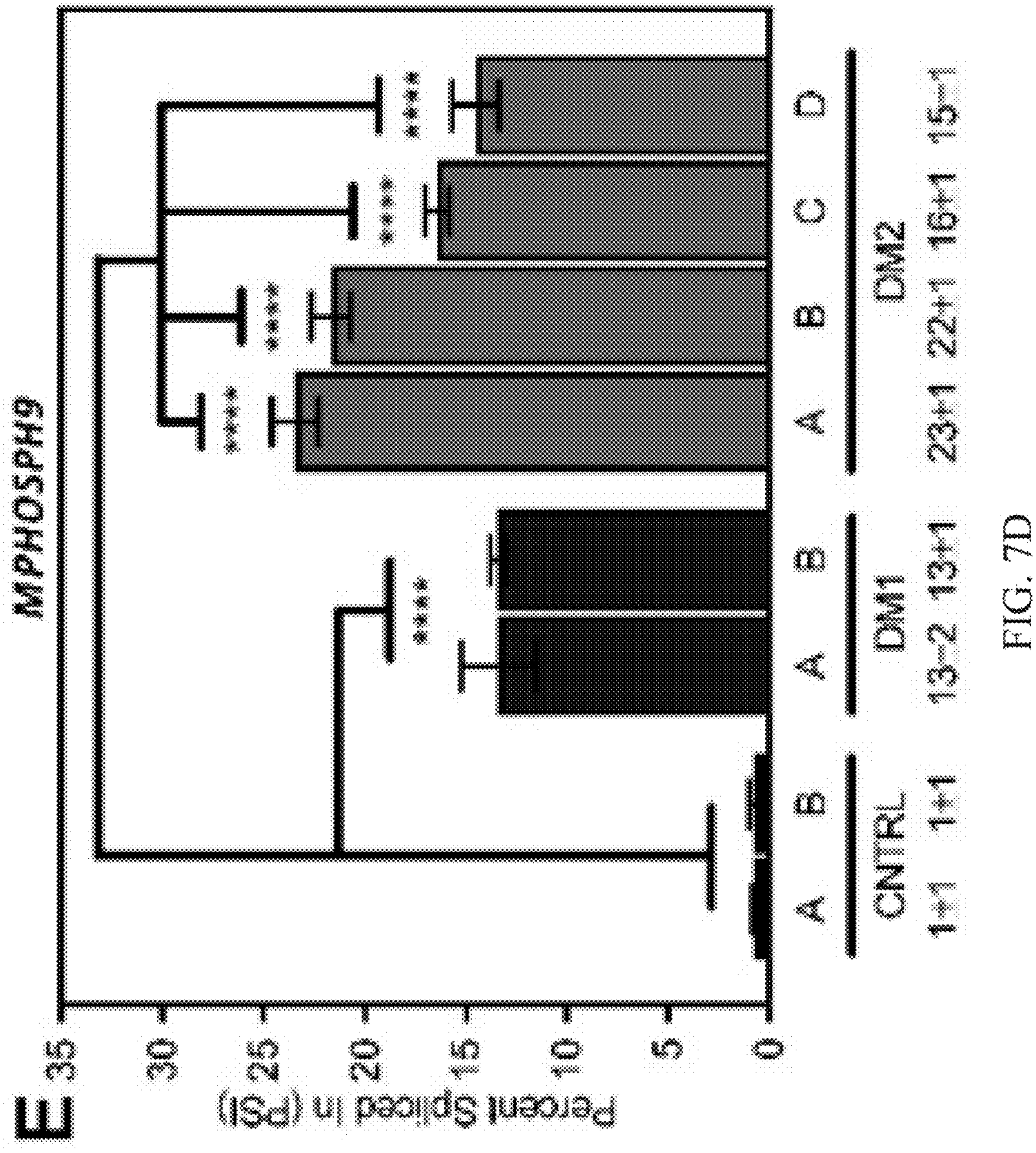
Figure 7E:
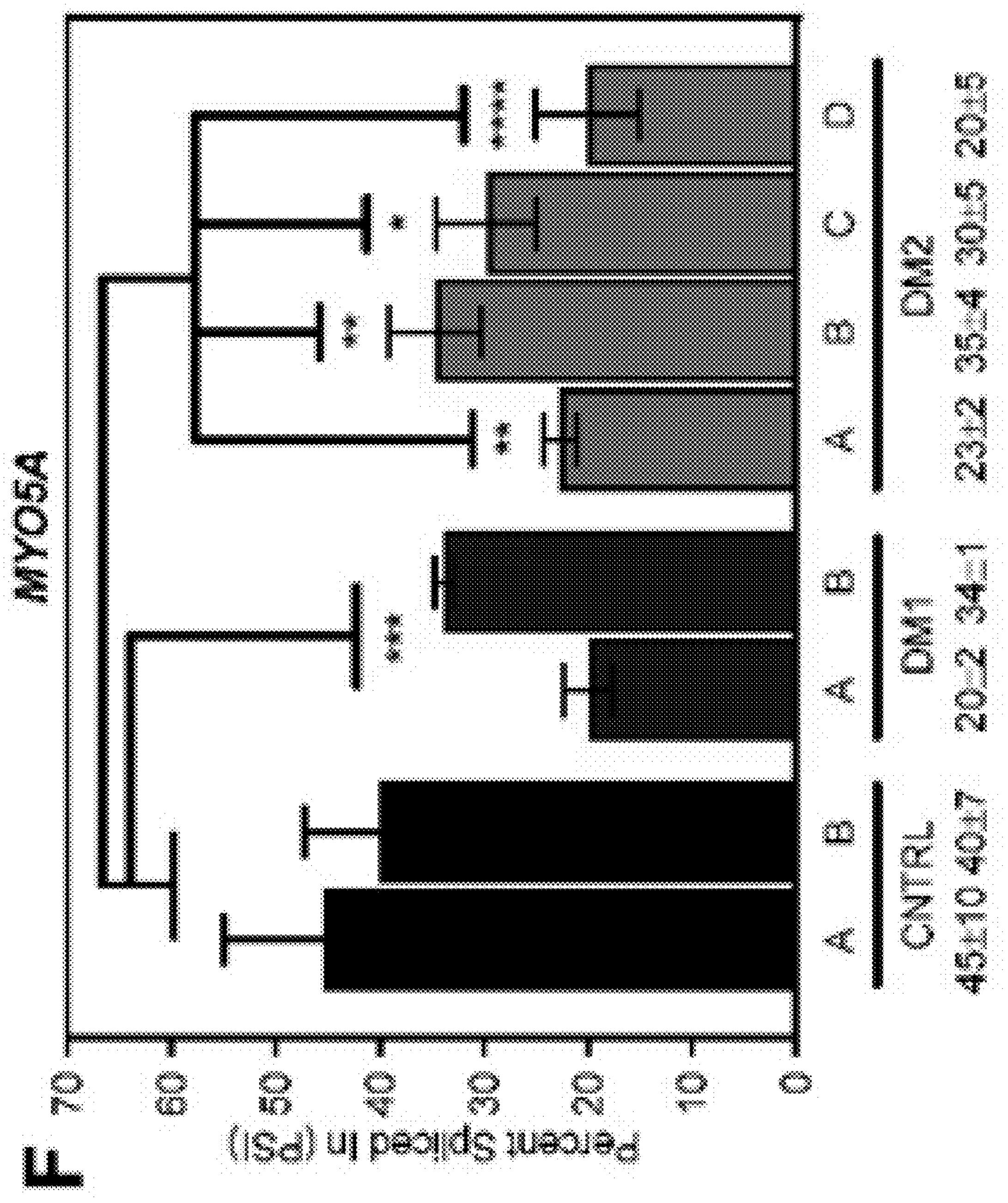
Figure 7F:
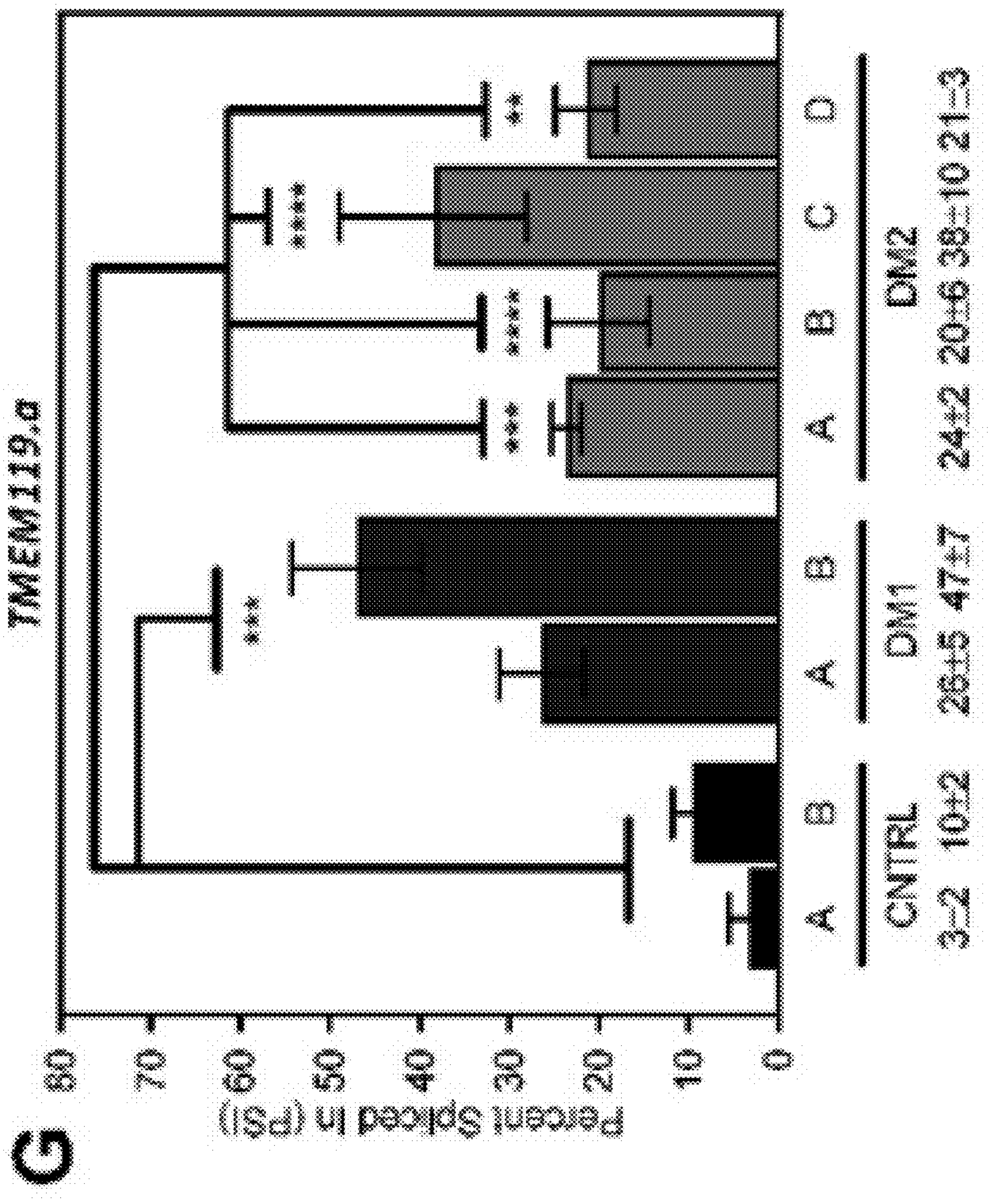

FIG. 7A-F depict patient-derived DMA and DM2 fibroblasts displaying molecular markers of disease. FIG. 7A depicts FISH analysis control, DM1, and DM2 fibroblast against CU(G)G RNA using either Cy3-(CAG)8 or -(CAGG)6 probes (red). FIG. 7B depicts RNAseq alternative exon (AE) event analysis showing unique and overlapping events in DM1 and DM2 fibroblasts. FIG. 7C depicts RT-PCR analysis of alternative exon splicing in DM1 and DM2 fibroblasts for (FIG. 7C) SYNE1, FIG. 7D MPHOSPH9, FIG. 7E MyO5A, and FIG. 7F TMEM119.a expresses as percent spliced in (PSI). Mean % spliced in +/−SD is noted below (ANOVA two-tailed test, *p less than 0.05, p less than 0.01, <P less than 0.001, **P is less than 0.0001.

DM splicing panel analysis: MPCs are evaluated starting with HM19A &19B in control and DM cells using a 5-point dose-response treatment. Data from the characterization of multiple DM1 & DM2 fibroblast supports this splicing panel and the utility of fibroblasts as a screening tool (See FIGS. 7A-E). A validated RT-PCR panel of DM1-specific (NCOR2, PHKA1, and SYNE1.a), DM2-specific (CD46, CPNE1, MYL6, and SYH3YL.c) and shared alternative cassette exon splicing events (See e.g., FIG. 7C-F: SYNE1, MYPHOSPH9, MYO5A, TMEM119.a) is used to evaluate the degree of mis-splicing rescue for each lead MPC.

DM-relevant gene expression changes: Expression of DMPK and CNBP is measured in control and DM patient cells via RT-qPCR32,51. The abundance of CUG/CCUG expansion RNA and ribonuclear foci is determined using Northern blotting and fluorescence in situ hybridization (FISH). MBNL1/2 and RBFOX1 transcript abundance and protein abundance/distribution will be determined through RT-qPCR and western blotting/immunofluorescence respectively.

Distinguish effects on transcription from RNA turn-over: To complement binding studies (See e.g., FIG. 1, Step 1) and functionally distinguish the relative contribution of MPC treatment on toxic CUG/CCUG RNA production and turnover, a 5-Ethynyl Uridine (EU) pulse labelling study is conducted. Pulse labelling followed by nascent RNA isolation and coupled to RT-qPCR is performed on MPC treated control and DM patient fibroblasts (DM1/2) and myoblasts differentiated into myotubes (DM1 only). By varying EU pulse times, one is able to differentiate effects of transcription from RNA turn-over as done previously. To specifically probe for a potential effect on transcription, transcription run-on assays are performed to determine the sequence determinants and stage(s) of transcriptional inhibition. DNA templates with CTG/CCTG repeats are incubated with HeLa nuclear extracts and transcription is measured by incorporation of radioactive (P32) CTP in the presence and absence of MPCs. Concentrations of MPCs tested will be informed by effective binding to CTG/CCTG repeats (See e.g., FIG. 1, step 1) and in vivo performance (See e.g., FIG. 1 steps 2 and 3). Transcription time courses are performed to measure transcription rates. Gel electrophoresis of transcribed products reveals whether abortive or paused products increase with MPC treatment. To test for effects on toxic CUG/CCUG RNA turn-over independent of transcription, HeLa cells are transfected with in vitro transcribed RNA as done previously, followed by MPC treatment. Toxic CUG/CCUG RNA abundance will be measured using RT-qPCR and ribonuclear foci will be evaluated with FISH.

On- and off-target transcriptomic effects: RNA sequencing (RNAseq) is a robust approach to globally assess changes to the transcriptome and therefore specificity of small molecules. To assess specificity of HM19A/HM19B and their analogs, a treatment is performed on patient-derived control and DM fibroblasts (DM1&2, See e.g., FIGS. 7A-7E) & myotubes (DM1 only), with monitoring of subsequent changes in gene expression and alternative splicing using RNAseq. For all three cell lines, furamidine treatment partially rescues mis-splicing and is used as a positive control. RNAseq data is analyzed as done previously. Briefly, RNA from patient-derived cell lines is isolated with Trizol and converted to ribosomal RNA-subtracted RNAseq libraries (KAPA Biosystems) and sequenced (Illumina NextSeq 500). Hisat2 is used to map reads, DESeq2 to quantitate gene expression, and rMATS to quantitate splicing. A minimum of three biological replicates is performed for all small molecule experiments. Small molecule concentrations identified as described above will inform concentrations used for RNAseq. To understand off-target effects of small molecules and potential toxicity, differentially expressed transcripts are analyzed for enriched motifs and gene ontology terms.

Effects on cellular health: To monitor the overall health of cells, treated vs. untreated control and DM patient fibroblast and myoblast/myotube lines are tested across a dose range where one observes a reduction in toxic CUG/CCUG RNA levels and rescue of mis-splicing. Cell health is monitored using the lactate dehydrogenase (LDH) and methylthiazol tetrazolium (MTT) assays, to measure membrane integrity (cell death) and metabolic activity (cell viability), along with monitoring rates of cell growth. Mutagenicity is assessed using the Ames test. Alterations in cell death, cell viability and rates of cell growth and mutagenicity is combined with data from control cells to determine the overall effect on cell health due to MPC treatment. As shown in FIGS. 2A-2E, HM19B rescues splicing at more than 50-fold lower concentrations than at concentrations where cell death is starting to be observed.

MDR1-MDCK monolayer assay: The MDR1-MDCK monolayer is widely used across the pharmaceutical industry as a cellular model for P-glycoprotein (P-gp) mediated transport and to predict brain uptake potential. P-gp is one of the most well-recognized efflux transporters and highly expressed in the capillaries of the blood brain barrier (BBB), which prevents penetration of its substrates. To measure BBB penetration, transwell inserts are seeded with MDCK cells for 5-7 days prior to use whereby permeability assays are initiated by replacing medium in the donor chamber with candidate MPC-containing transport medium with also contains a paracellular integrity marker (midazolam) and P-gp marker (digoxin). After 1 h of incubation at 37° C. in a tissue culture incubator, samples are removed from both apical and basolateral chambers and analyzed for MPC and digoxin by UPLC-MS/MS and midazolam by fluorescence microplate reader. Transepithelial electrical resistance (TEER) values will be determined to confirm the integrity of the monolayers for each insert. In some embodiments, apparent permeability (Papp) and efflux ratio may be calculated for each candidate MPCs and compared to baseline controls (furamidine and DB829). This assay has been previously used to predict brain uptake potential for several diamidines.

Rigor and Reproducibility: In embodiments, all experiments are done minimally in triplicate with the necessary statistical analyses to ensure all results are robust and reproducible. In embodiments, all drug treatments include multiple independent preparations to minimize batch effects. Cell lines currently include at least 1 male and 1 female, which will be expanded when new lines become available to minimize gender bias and are age-matched. RNAseq experiments will be filtered for significance with stringent false discovery rate (FDR) cutoffs (typically $p<0.01$ and $FDR<0.1$).

Outcomes and Alternative Approaches: The preliminary data supports a cellular role for HM19A & HM19B on toxic RNA pathogenesis (See e.g., FIGS. 2A-2E). In embodiments, this effect at least partially occurs through IMPEDE, and the MOA is systematically evaluated to determine the relative contribution of the role of transcription, RNA turnover and other mechanisms. MPC treatment could also alter MBNL/RBFOX gene expression which would affect splicing outcome independent of a direct effect on CUG expansion RNA. Understanding these outcomes informs our model-design-test cycle and aid in functionalizing further MPC derivatives. To date, the inventors have been successful in rapidly developing a series of MPC compounds (See e.g., FIGS. 5A and 5B) including HM19A and HM19B.

Based on initial DM patient cell and mouse model results (See e.g., FIGS. 2A-2E), both of these compounds show efficacy. An important concern is any potential toxicity that could be induced by off-target effects. Based on extensive previous experience with the diamidine class (refs), the inventors identify potential areas of concern when designing the new MPC scaffolds. For example, it is noted that altering the length of the side and/or end groups (HM19A & HM19B) resulted in increased potency accompanied by lowered toxicity at and beyond the active dose range (See e.g. FIGS. 2A-2E). Another high priority is solubility and cell uptake. While our HeLa and fibroblast DM cell lines are relatively permissive to drug treatment at least partly owing to passive drug uptake during cellular division, myotubes pose a greater challenge due to the post-mitotic state where cellular and nuclear membrane breakdown is not occurring and thus myotube testing is an important component of our pipeline. Reversal of DM cellular and molecular hallmarks in myotubes at lower MPC doses provides strong validation of potential bioactivity. Continued parallel cellular testing of a range of MPC modifications including lengthening the core, side or end groups as well as testing asymmetric configurations will inform specific structure-function outcomes including off-target-driven toxicity and solubility/drug uptake for our MPC series. This data enables us to relate specific modules on our MPC scaffolds to the cellular outcomes in order to rationally design diverse MPC leads to accompany an existing series including promising initial hits HM19A & HM19B for testing in DM animal models.

To determine the bioavailability, splicing rescue, and therapeutic potential of lead candidate MPCs in two DM1 mouse models Rationale and preliminary data: Understanding the bioavailability, splicing rescue and therapeutic potential of the MPCs of the present disclosure is critical for forging a path towards pre-clinical studies. In vivo testing approach utilizes different DM1 mouse models to target different tissue systems: skeletal muscle using the well-characterized HSALR mouse55 and brain using the recently developed DMPK480/480 mouse. The HSALR/LR mouse and recently described HSAXLR mouse are well characterized pre-clinical models for DM1 skeletal muscle features. These models recapitulate key RNA mis-splicing and other molecular (RNA foci), histopathological (central nuclei and split fibers) and pathological (myotonia, reduced strength) features seen in DM patient skeletal muscle. While these transgenic mice are excellent models of muscle involvement, they lack DMPK's tissue specificity, developmental timing, and spatial expression thereby restricting pre-clinical non-muscle implications. In contrast the recently characterized Dmpk480/480 model incorporates, via CRISPR/Cas9-mediated genome editing, 480 CTG repeats in the endogenous Dmpk context35. This model has in vivo disease features in the choroid plexus, including RNA foci, MBNL1 mis-localization and RNA splicing defects. Testing compounds in both models enables a better understanding of therapeutic impacts across tissue system but also the compound's ability to penetrate the blood-brain-barrier (BBB). The latter is an important therapeutic criterion for drugs aiming to address the cognitive disabilities that are of significant concern to DM patients and their families. These two models provide an excellent framework for understanding our lead MPC's therapeutic potential.

Figure 8A:
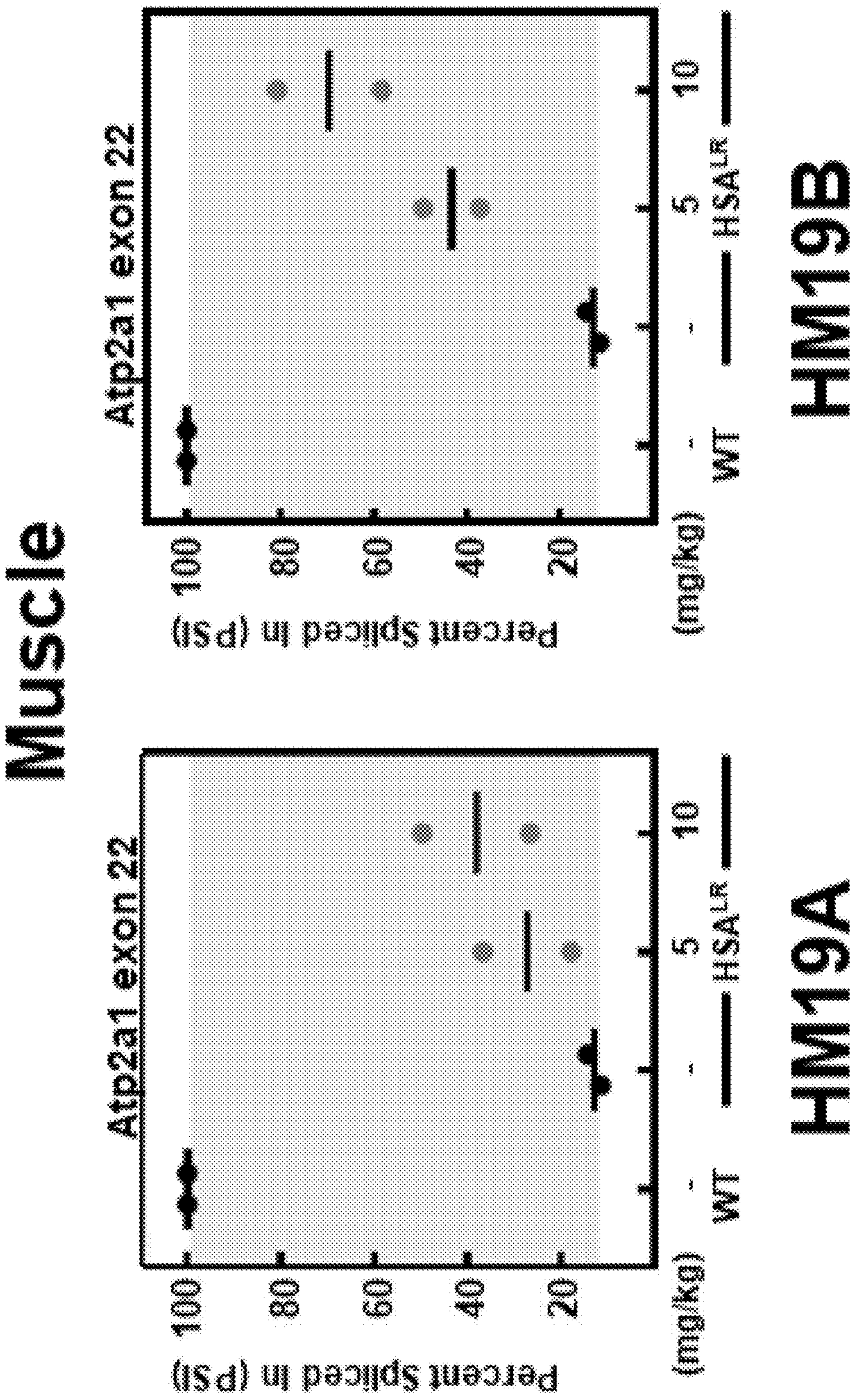
FIGS. 8A-8C depict a polycyclic compound of the present disclosure showing rescue in various mouse models.
Figure 8B:
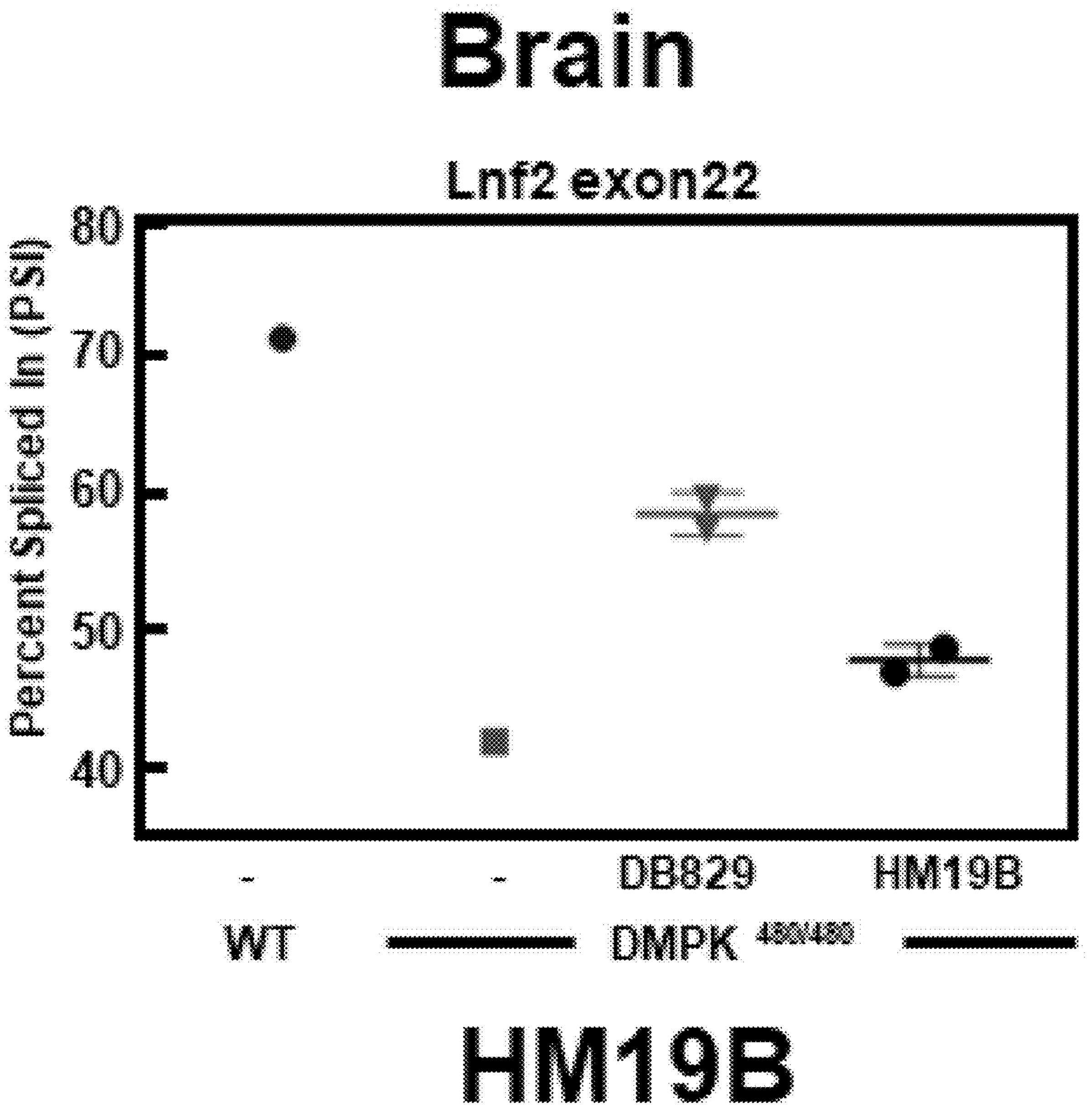
Figure 8C:
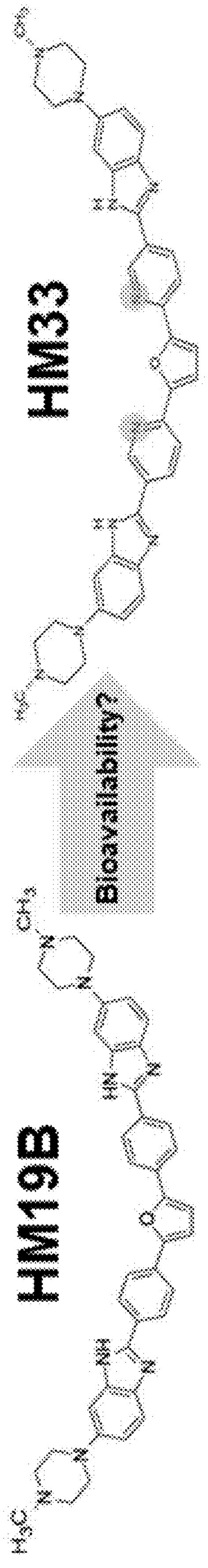

Preliminary data indicates that HM19A and HM19B are capable of significantly rescuing mis-splicing in patient-derived cell lines as well as the HSALR mice (See e.g., FIG. 8A-8C). FIG. 8 HM198 shows rescue in both $HSA^{LR/LR}$ and $Dmpk^{480/480}$ DM mouse models. Pilot experiments showing RT-PCR splicing rescue of FIG. 8AAtp2a1 exon 22 (responsive in muscle) in TA muscle of $HSA^{LR/LR}$ mice (N=2) treated at 5 or 1 Omg/kg with HM19A and HM19B for 7 days; and FIG. 8B Lnf2 exon22 (responsive in choroid plexus) in choroid plexus of $Dmpk^{480/480}$ mice (N=2) treated at 10 mg/kg with DB829 and HM19B. FIG. 8C presents reduced rescue of HM198 compared to DB829 in the CNS suggest the need for bioavailability improvements. New MPCs, including HM33, are being systematically designed to study bioavailability. Early preliminary data shows HM19B is also capable of rescue in the Dmpk480/480 mice (See e.g., FIG. 8A-8C). Systematic modification of current MPCs (See e.g., FIGS. 5A and 5B) is used to assess the contribution of each change to bioavailability with the goal of improving BBB and other organ penetration. Overall while these results are promising, further detailed characterization of splicing events, off-target effects, histopathology and bioavailability fully assesses HM19A, HM19B and other MPCs therapeutic potential.

To determine the in vivo bioavailability, splicing rescue and therapeutic potential of our lead candidate MPCs, a parallel approach is taken. Based on preliminary data, one pursues long-term HSALR studies with HM19A and HM19B combined with short-term Dmpk480/480 studies. Data from these studies will feed refinement efforts (See e.g., FIG. 1, step 1) and experimental approach (See e.g., FIG. 1 step 2). Second, the best-in-class MPCs are screened in short-term dose-response in vivo studies in both HSALR and Dmpk480/480 with the goal of identifying 2-5 lead candidates for matching long-term in vivo studies. This approach improves an understanding of the candidates' impact in complex tissue systems and in vivo data necessary to support additional pre-clinical efficacy studies.

A note on HSA-based models: There is extensive experience with the HSALR/LR having tested numerous small molecules in this mouse model. The recently developed HSAXLR with a repeat tract twice as long as the original HSALR (440 vs. 220) results in highly distinct CUG-repeat RNA nuclear foci, muscle myotonia, and accumulation of CUG-repeat expansion RNA in the heterozygous state. To maintain data continuity, several candidate MPCs and baseline compounds are tested in both HSALR/LR and HSAXLR, with remaining mouse model testing demonstrating robust and reproducible data consistent with previous findings.

Short-term Studies: To select excellent candidates for long-term studies, cohorts (N=6) of one-month old age- and gender-matched animals from both muscle (homozygous HSALR/LR or heterozygous HSAXLR) and brain (Dmpk480/480) mouse models are treated. Both transgenic (N=6) and matching wild-type (N=6) mice are treated every two days at 3 different concentrations of lead MPCs (2, 5 and 10 mg/kg) or PBS via IP injection for a period of 1 week. The 48-hour injection schedule and starting concentrations are based upon previous treatment regimens and preliminary pharmacokinetic analysis. However, the schedule or treatments is subject to change depending upon the candidate compound's history and performance in e.g., Steps 1 and 2 of FIG. 1. After 1 week of treatment, mice are tested for health (body weight, body condition score) then sacrificed, and muscle tissue (tibialis anterior, vastus lateralis, liver, kidney & brain) harvested and tested for in vivo changes in molecular (foci, splicing and MBNL1 colocalization) and histopathological features (central nuclei, HSA-based models only). To assess molecular features, frozen muscle samples are tested for: mis-splicing changes (RT-PCR and RNAseq); transgene and endogenous DMPK expression (qRT-PCR); off-target effects (RNAseq); RNA foci (FISH); MBNL1 colocalization (FISH/IF); CLCN1 staining (IF); and central nuclei (H&E). Frozen muscle and brain samples from each mouse model are analyzed by UPLC-MS/MS to determine preliminary bioavailability, which is correlated with molecular activity (muscle only for HSA-based and brain only for DMPK480/480) to assess therapeutic potential. Selection of lead candidates is determined based on each drug's or active agent's dose-response (short term & in cellulo) and performance for splicing rescue (@ 1 μM), cell-based toxicity (@ 1 μM), and RNAseq off-target effects (less than 2%) in comparison to baseline furamidine values.

Long-term studies: To determine long-term bioavailability, efficacy, and therapeutic potential, cohorts of one-month old male and female animals are examined from both muscle (homozygous HSALR/LR or heterozygous HSAXLR) and brain (Dmpk480/480) mouse models. Both transgenic (N=20) and wild-type (N=20) mice are treated every two days at 3 different concentrations of lead candidates or PBS via IP injection for a period of 3 months. The treatment route (injection vs oral), starting concentrations and schedule is determined by each candidate's performance in e.g., steps 1-3 in FIG. 1, with a 48-hour injection schedule serving as the default schedule. As with the short-term study, the cohorts are age- and gender-matched to ensure adequate rigor and reproducibility. During treatment mice are monitored for signs of acute toxicity, such as tremors, lachrymation, excess salivation or urination, diarrhea and irritation (scratching at injection site or general discomfort). Signs of toxicity during treatment are monitored either daily based on changes in cage behavior, weekly via weight changes or monthly via blood sample analysis.

Long-term efficacy and therapeutic potential: A cohort of transgenic and wildtype mice (N=6) is sacrificed following each 4-week period of treatment (3 & 4 months) and at the experimental end-point (5 months). To examine phenotypic efficacy, at each time point mice is tested for health (body weight, body condition score) and myotonia (HSA-based only, grip strength and EMG). To examine molecular efficacy, following behavior assessment each mouse will be sacrificed and tissue (tibialis anterior, vastus lateralis, heart, kidney, liver, brain and blood) harvested and stored frozen. Muscle tissue (TA & VL) is tested for in vivo changes in molecular and histopathological activity to measure efficacy of treatment as outlined above and toxicity, if any. RNA is extracted from frozen muscle and brain samples and tested for splicing changes (RT-PCR and RNAseq) as well as transgene and/or endogenous Dmpk expression levels (qRT-PCR). Matching frozen muscle tissue will be sectioned and tested by immunofluorescence for RNA foci (FISH), MBNL1 colocalization (FISH/IF), and CLCN1 staining (IF), as well as for muscle histopathology (HSA only) via H&E staining for central nuclei.

Muscle and brain RNAseq data is used to examine global off-target effects, gene expression change and variations in alternative splicing. For transcriptomics analysis, RNA is extracted from muscle or brain biopsies using the AllPrep DNA/RNA/protein kit (Qiagen), libraries prepared using Ultra II Directional RNA Library Prep Kit (Illumina) and sequenced on an Illumina NovaSeq 6000. For gene expression analysis, Salmon is applied to map reads to the hg38 genome followed by analysis with DESeq2 package in R for differential gene expression analysis. For splicing analysis, STAR will be applied to map the reads to the hg38 genome and Salmon will be used for gene expression analysis. Alternative splicing analysis will be done using rMATS. Pathways analysis will be done using Enrichr.

Bioavailability: To test drug distribution and bioavailability, extracts from frozen tissue samples (muscle, heart, kidney, liver, brain, blood) are homogenized and extracted for UPLC-MS/MS as previously described. While molecular disease features are only evident in muscle (HSA-models) or brain (DMPK480/480), one utilizes other lesser and/r non-affected tissues to examine compound bioavailability. This data informs further small molecule optimization (e.g. FIG. 1, steps 1 and 2) and future pre-clinical studies. Bioavailability in filtration organs (kidney & liver) is correlated with any observed signs of toxicity to understand the distribution and potential organ toxicity. Taken together this data provides important information for additional medicinal chemistry optimization as well as future pre-clinical studies.

Randomization and Blinding: To minimize effects of subjective bias, animal handling and treatment are separated from analyses of processed tissue and extracted RNA. Animals are assigned unique identifiers by treatment group and subsequent tissue and molecular analyses are performed by separate investigators in a blinded manner.

Rigor and Reproducibility: Animal experiments are performed with triplicate technical replicates to ensure robust reproducibility in analyses from each treatment cohort. Means of treatment groups with standard deviation are calculated and compared to controls (vehicle treatment) using the appropriate statistical measures. Both males and females are used for treatment studies with littermate treatment controls being applied whenever possible.

Outcomes and Alternative Approaches: Dose-responsive splicing rescue is observed with low toxicity and modest off-target effects in both muscle and brain animal models with candidate MPCs. Long-term treatment shows a cumulative effect in both activity and potentially off-target effects. Examining effects in both muscle and brain from 2 independent animal models in parallel provides a better pre-clinical assessment. The inventors are not aware of a characterized DM2 mouse model, which limits the potential for parallel diseases studies.

What is claimed is:

1. A method of treating a medical condition involving expanded CTG and/or CCTG repeats in a subject in need thereof, said method comprising, administering to the subject an effective amount of at least one polycyclic compound selected from the group consisting of

HM33

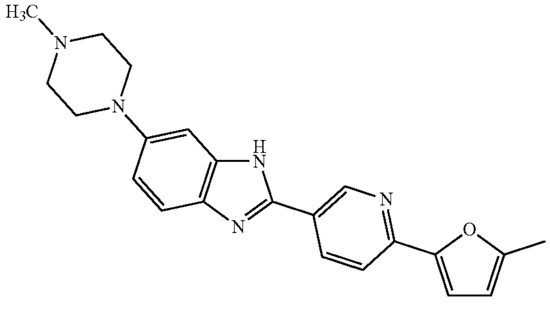

-continued

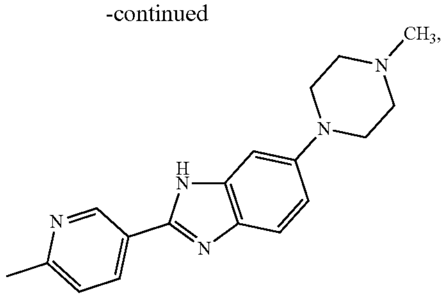

HM19A

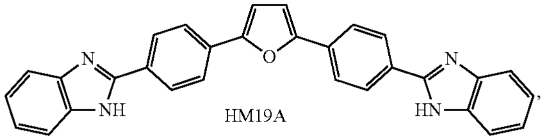

HM19A and

HM19B

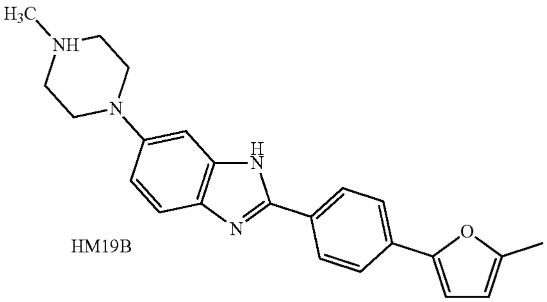

HM19B

-continued

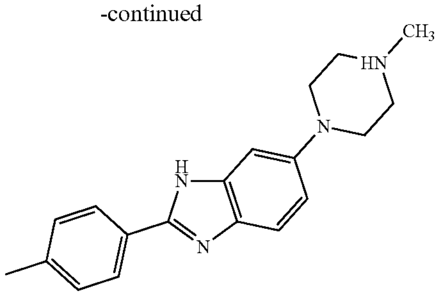

or a pharmaceutically acceptable salt or solvate thereof.

2. The method of claim 1, wherein the medical condition is DM Type 1, DM Type 2, or combinations thereof.

3. The method of claim 1, wherein the effective amount is an amount sufficient to block one or more harmful effects of an expanded CTG repeat in a DMPK gene (DM type 1) or an expanded CCTG repeat in a ZNF9 gene (DM type 2).

4. A method of inhibiting microsatellite promoted expression of one or more deleterious expansions by targeting expanded CTG and CCTG DNA repeats in a subject in need thereof by administering to the subject a therapeutically effective amount of a polycyclic compound of claim 1.

5. A method of treating a medical condition involving expanded CTG repeats in a subject in need thereof, said method comprising, administering to the subject an effective amount of at least one polycyclic compound selected from the group consisting of:

HM33

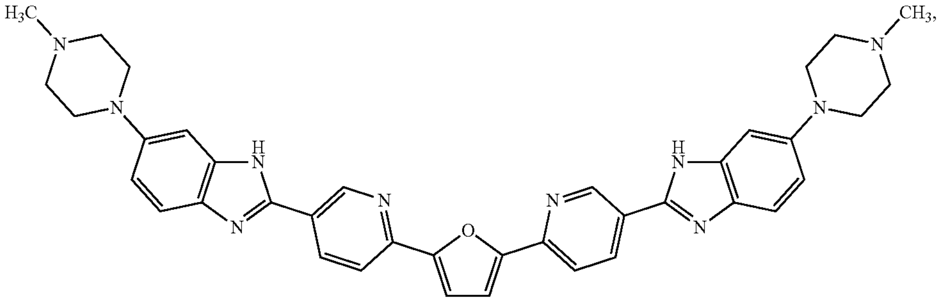

HM19A

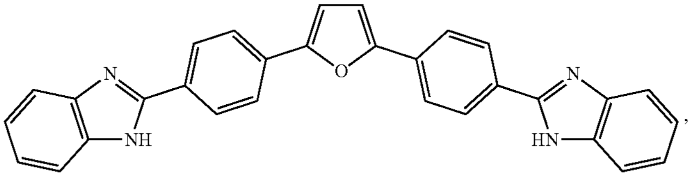

, and

-continued

HM19B

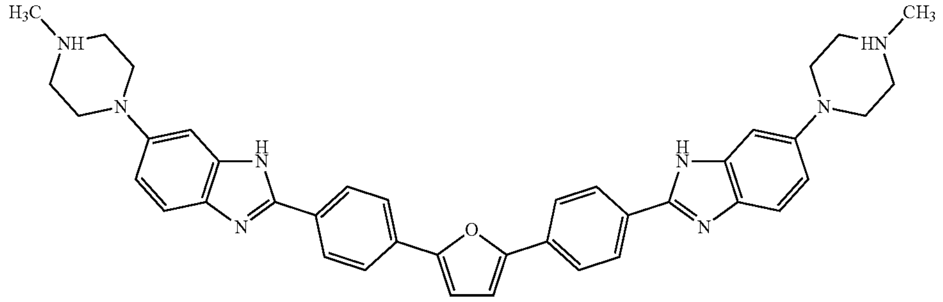

or a pharmaceutically acceptable salt or solvate thereof, wherein the medical condition is Type 1 DM.

6. The method of claim 5, wherein the effective amount is an amount sufficient to block one or more harmful effects of an expanded CTG repeat in a DMPK gene (DM type 1).

7. A method of inhibiting expression of one or more deleterious microsatellite expansions by targeting expanded CTG DNA repeats in a subject in need thereof by administering to the subject a therapeutically effective amount of a polycyclic compound of claim 5.

* * * * *